United States Patent [19]

Yamada et al.

[11] 4,160,087
[45] Jul. 3, 1979

[54] N-ACYLAMINO-α-ARYLACETAMIDO CEPHALOSPORINS

[75] Inventors: Hirotada Yamada, Nishinomiya; Kousaku Okamura, Takarazuka; Hisao Tobiki, Kobe; Norihiko Tanno, Ashiya; Kozo Shimago, Toyonaka; Takenari Nakagome, Nishinomiya; Toshiaki Komatsu, Takarazuka; Akio Izawa, Kawanishi; Hiroshi Noguchi, Nishinomiya; Kenji Irie, Takarazuka; Yasuko Eda, Toyonaka, all of Japan

[73] Assignee: Sumitomo Chemical Company, Limited, Osaka, Japan

[21] Appl. No.: 795,596

[22] Filed: May 10, 1977

Related U.S. Application Data

[62] Division of Ser. No. 611,104, Sep. 8, 1975.

[30] Foreign Application Priority Data

| Sep. 6, 1974 | [JP] | Japan | 49-103183 |
| Sep. 19, 1974 | [JP] | Japan | 49-108428 |
| Sep. 19, 1974 | [JP] | Japan | 49-108429 |
| Mar. 20, 1975 | [JP] | Japan | 50-33824 |

[51] Int. Cl.² .................. C07D 501/34; A61K 31/545
[52] U.S. Cl. ...................................... 544/28; 544/27; 424/246
[58] Field of Search ........................................... 544/28

[56] References Cited

U.S. PATENT DOCUMENTS

| 3,867,380 | 2/1975 | Dunn et al. | 544/26 |
| 3,931,160 | 1/1976 | Dunn | 544/26 |
| 3,954,734 | 5/1976 | Doub et al. | 544/27 |
| 4,015,000 | 3/1977 | Kocsis et al. | 544/28 X |
| 4,041,161 | 8/1977 | Kocsis et al. | 544/28 X |

*Primary Examiner*—Donald G. Daus
*Assistant Examiner*—Diana G. Rivers
*Attorney, Agent, or Firm*—Sughrue, Rothwell, Mion, Zinn and Macpeak

[57] ABSTRACT

A cephalosporin derivative of the formula (I),

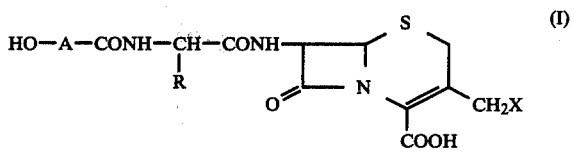

wherein A is a mono- or polycyclic heteroaromatic ring, which contains at least one nitrogen atom as a hetero atom and which may be substituted with one or more substituents; R is a phenyl group substituted with at least one substituent selected from the group consisting of an amino group, a hydroxy group, a ureido group and a hydroxymethyl group; and X is an —OCOCH$_3$ group or an —S-Het group in which Het is a 5- or 6-membered heterocyclic ring containing one to four hetero atoms selected from the group consisting of nitrogen, oxygen and sulfur atoms which may be substituted with one or more substituents, and the non-toxic pharmaceutically acceptable salts thereof which are useful as an antimicrobial and prepared by the reaction of a compound of the formula (II),

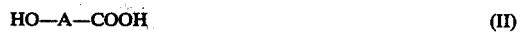

wherein A is as defined above, or a reactive derivative thereof, with a compound of the formula (III),

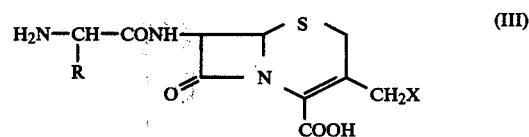

wherein R and X are as defined above, or a derivative thereof.

1 Claim, No Drawings

N-ACYLAMINO-α-ARYLACETAMIDO CEPHALOSPORINS

This is a division of application Ser. No. 611,104 filed Sept. 8, 1975.

BACKGROUND OF THE INVENTION

1. Field of the Invention

The present invention relates to a novel cephalosporin and to a process for the preparation thereof. More particularly, it relates to a novel cephalosporin of the formula (I),

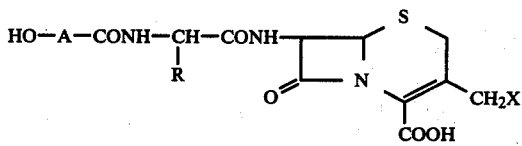

wherein A, R and X are as described hereinafter, the non-toxic pharmaceutically acceptable salts thereof and to the preparation thereof.

2. Description of the Prior Art

It is known that cephalosporin series compounds such as Cephalothin and Cefazolin are very effective and are widely used as chemotherapeutic agents for infectious diseases caused by gram-positive or gram-negative bacteria.

However, these cephalosporin series compounds have no effect on infectious diseases caused by *Pseudomonas aeruginosa* which has been spreading increasingly in recent years and is often very difficult to cure. Cephalosporin series compounds which are effective against *Pseudomonas aeruginosa* are not yet commercially available.

SUMMARY OF THE INVENTION

Accordingly, in one embodiment, the present invention provides compounds of the formula (I)

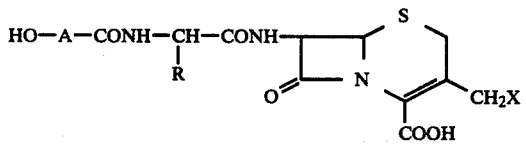

wherein A is a mono- or polycyclic heteroaromatic ring, which contains at least one nitrogen atom as a hetero atom and which may be substituted with one or more substituents; R is a phenyl group substituted with at least one substituent selected from the group consisting of an amino group, a hydroxy group, a ureido group and a hydroxymethyl group; and X is an —OCOCH$_3$ group or an —S-Het group in which Het is a 5- or 6-membered heterocyclic ring containing one to four hetero atoms selected from the group consisting of nitrogen, oxygen and sulfur atoms which may be substituted with one or more substituents, and the non-toxic pharmaceutically acceptable salts thereof which are useful as antimicrobial agents.

In another embodiment the invention provides a pharmaceutical composition containing at least one compound of the formula (I) or a non-toxic pharmaceutically acceptable salt thereof (I) as an active ingredient.

In a further embodiment the invention provides a process for the preparation of the compounds of the formula (I) and the non-toxic pharmaceutically acceptable salts thereof.

DETAILED DESCRIPTION OF THE INVENTION

In the formula (I), A is a mono- or polycyclic heteroaromatic ring containing at least one nitrogen atom as the hetero atom, and examples include quinoline, isoquinoline, cinnoline, naphthyridine, quinoxaline, pyrazolopyridine, pyridopyrazine, thiazolopyrimidine, pyridopyrimidine, pyridine, pyrimidine, pyridazine, triazine, pyrazine and the like. These heterocyclic rings can be substituted with one or more substituents selected from the group consisting of a halogen atom, a lower alkyl group, a lower alkoxy group, a lower alkanoyl group, a lower alkoxycarbonyl group, a lower alkylthio group, a mercapto group, a hydroxy group, a lower alkoxymethyl group, a cyano group, a nitro group, a lower alkylsulfonyl group, an arylsulfonyl group, a sulfamoyl group, a carbamoyl group, an aryloxycarbonylamino group, an acetoacetylamino group, a lower alkylamino group, a lower dialkylamino group, a lower haloalkyl group, a lower alkenyl group, an aryl group, a cycloalkyl group and the like in addition to the hydroxyl group.

In the formula (I), the R preferably is a substituted phenyl group of the formula

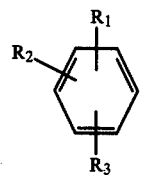

wherein R$_1$ is a ureido group, a hydroxyl group, an amino group, or a hydroxymethyl group; R$_2$ and R$_3$ each is a hydrogen atom, a chlorine atom, a bromine atom, a fluorine atom, an iodine atom, a nitro group, a di-lower alkylamino group, a lower alkanoylamino group, an amino group, a hydroxyl group, a lower alkanoyloxy group, a lower alkyl group, a lower alkoxy group, a trifluoromethyl group, a hydroxymethyl group, a sulfamyl group or the like.

In the formula (I), X is an —OCOCH$_3$ group or an —S-Het group wherein —Het is a five- or six-membered heterocyclic ring containing one to for hetero atoms selected from the group consisting of nitrogen, oxygen and sulfur atoms. The heterocyclic ring may be substituted with a (C$_1$–C$_4$)alkyl group, a hydroxy group, a lower alkoxy group, a mercapto group or a hydroxymethyl group. Examples of suitable heterocyclic rings incude, for example, 1-methyl-tetrazol-5-yl, 2-methyl-1,3,4-thiadiazol-5-yl, 1,2,3-triazol-5-yl, 1,2,4-triazol-3-yl, tetrazol-5-yl, 2-methyl-tetrazol-5-yl, 2-mercapto-1,3,4-thiadiazol-5-yl, 2-hydroxymethyl-1,3,4-oxadiazol-5-yl, 2-hydroxymethyl-1,3,4-thiadiazol-5-yl, 2-aminomethyl-1,3,4-thiadiazol-5-yl, 3-hydroxypyridazin-6-yl, 1,3,4-thiadiazol-5-yl, 2-methylamino-1,3,4-thiadiazol-5-yl and the like.

Examples of non-toxic pharmaceutically acceptable salts derived from the compounds of formula (I) include the sodium salt, the potassium salt, the calcium salt, the magnesium salt, the triethylamine salt, the diethanolamine salt, the morpholine salt, the procaine salt, the L-arginine salt, the L-lysine salt and the like.

The α-carbon atom of the side chain (phenylglycine moiety) attached to the 7-position of the formula (I) is an asymmetric carbon atom and therefore two optically active isomers exist. These two isomers (D-diastereomer and L-diastereomer) and the DL-form are included within the scope of the present invention, but the D-diastereomer is preferred.

As used herein, the term "lower alkyl" preferably means a straight or branched alkyl group or alkyl moiety having one to four carbon atoms.

Ther term "lower alkoxy" preferably means a straight or branched alkoxy group or moiety having one to four carbon atoms.

The term "lower alkanoyl" preferably means an alkanoyl group or moiety having two to five carbon atoms.

The term "halogen" means fluorine, chlorine, bromine, and iodine.

The term "aryl" preferably includes a phenyl group and a pyridyl group and the term "arylsulfonyl" preferably includes a phenylsulfonyl group and a pyridylsulfonyl group.

The term "aryloxycarbonylamino" preferably includes a phenoxycarbonylamino group.

The term "haloalkyl" means a halogen-substituted alkyl group having one to four carbon atoms.

The term "lower alkenyl" preferably includes an alkenyl group having up to four carbon atoms.

The term "cycloalkyl" means a cycloalkyl group having three to six carbon atoms.

The compound of the formula (I) of the present invention can be prepared by reacting a carboxylic acid of the formula (II),

HO-A-COOH     (II)

wherein A is as defined above, or a reactive derivative thereof, with a compound of the formula (III)

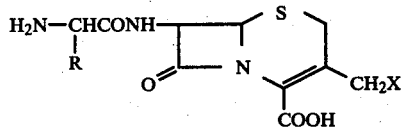

(III)

wherein R and X are as defined above, or a salt or derivative thereof, and when X is an —OCOCH$_3$ group, by further reacting the resulting product with a compound of the formula, SH-Het in which Het is as defined above, to convert X into an —S-Het group, if necessary.

Referring more particularly to the process, inert solvents which can be used in the reaction between the compounds of the formulas (II) and (III) include polar solvents such as dichloromethane, chloroform, acetone, tetrahydrofuran, dioxane, acetonitrile, methyl isobutyl ketone, ethyl alcohol, dimethylformamide, dimethylacetamide, dimethyl sulfoxide, nitromethane, hexamethylphosphoric triamide, sulfolane, and the like; non-polar solvents such as benzene, toluene, petroleum ether, n-hexane and the like; and a mixture thereof. These solvents can be used in combination with water.

The reactive derivatives of the compound (II) mean reactive derivatives of a carboxyl group, for example, an acid halide, an acid anhydride, an acid azolide, an active ester, an acid azide and the like. Referring more particularly to these reactive derivatives, examples include mixed acid anhydrides or symmetric acid anhydrides with acids such as dialkyl phosphoric acids, phenyl phosphoric acid, diphenyl phosphoric acid, dibenzyl phosphoric acid, halogenated phosphoric acids, dialkyl phosphorous acids, methanesulfonic acid, toluenesulfonic acid, naphthalenesulfonic acid, alkylcarbonates, aliphatic carboxylic acids (for example, pivalic acid, pentanoic acid, isopentanoic acid, 2-ethylbutanoic acid); acid azolides with imidazole, substituted imidazoles, dimethylpyrazole, triazole, and the like; and active esters such as cyanomethyl ester, methoxymethyl ester, vinyl ester, propargyl ester, p-nitrophenyl ester, 2,4-dinitrophenyl ester, trichlorophenyl ester, pentachlorophenyl ester, methanesulfonylphenyl ester, p-nitrophenylthio ester, carboxymethylthio ester, pyridyl ester, piperidyl ester, 8-quinolylthio ester, and esters with 1-hydroxy-2(1H)-pyridone, N-hydroxysuccinimide or N-hydroxyphthalimide.

Further, when the compounds of the formula (II) are used in the form of the free acid (or the salt thereof), it is preferred to carry out the reaction in the presence of coupling agents such as N,N'-dicyclohexylcarbodiimide, N-cyclohexyl-N-morpholinoethylcarbodiimide, N-cyclohexyl-N-(4-diethylaminocyclohexyl)-carbodiimide, N,N'-diethylcarbodiimide, N,N'-diisopropylcarbodiimide, N-ethyl-N-(3-dimethylaminopropyl)carbodiimide, N,N'-carbonyldi-(2-methylimidazole), pentamethyleneketene-N-cyclohexylimine, diphenylketene-N-cyclohexylimine, 2-ethyl-7-hydroxybenzisoxazolium salt, 2-ethyl-5-(m-sulfonyl)isoxazolium hydroxide inner salt, (chloromethylene)dimethyl ammonium chloride and the like.

As described above, those amidating agents which are generally used in the fields of peptide chemistry, penicillin chemistry and cephalosporin chemistry can be used in the present invention.

Examples of salts of compounds of the formula (III) include an alkali metal salt or an alkaline earth metal salt (for example, the sodium, potassium, calcium, etc. salts) of acids of the formula (III); organic amine salts (for example, trimethylamine, triethylamine, quinoline, collidine, etc. salts) of the acids of the formula (III); and organic sulfonic acid salts (for example, toluenesulfonic acid, naphthalenesulfonic acid, tetralinsulfonic acid, etc. salts) of the acids of the formula (III). Examples of derivatives of compounds of the formula (III) include carboxyl derivatives in which the carboxyl group is protected by esterification or amidation, or is in the form of the anhydride thereof.

The carboxyl-protecting group can be removed after the acylation reaction under mild conditions, for example, by a solvolysis such as a hydrolysis and an alcoholysis, a catalytic hydrogenation, a reduction, an oxidation, a nucleophilic substitution reaction, a photochemical reaction or an enzymatic reaction.

Examples of groups formed by suitable carboxyl protecting groups include a silyl ester, an organo-tin ester, a toluenesulfonyl ethyl ester, a p-nitrobenzyl ester, a benzyl ester, a phenacyl ester, a 2-furylmethyl ester, a diphenylmethyl ester, a substituted diphenylmethyl ester, a p-methoxybenzyl ester, a trityl ester, a benzoyloxymethyl ester, a lower alkanoyl oxymethyl ester, a dimethylmethyleneamino ester, a p-nitrophenyl ester, a methylsulfonylphenyl ester, a methylthiophenyl ester, a t-butyl ester, a 4-picolyl ester, an iodoethyl ester, a trichloroethyl ester, a phthalimidomethyl ester, a 3,4-dimethoxy or a 3,5-dimethylbenzyl ester, a 2-nitrobenzyl ester, a 2,2'-dinitrobenzyl ester, an acetyloxycarbonyl group, a trichloroethyl ester, a

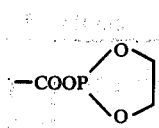

group, a —COON=CHR' group (in which R' is an alkyl group or an aryl group), a

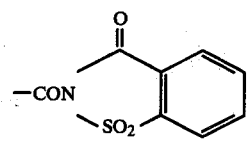

group and the like, which are formed from carboxyl protecting groups conventionally used in the fields of peptide, penicillin and cephalosporin chemistry.

In case of the silyl ester, other substituents of the compound of the formula (III), if any, such as a hydroxy group or an amino group may be silylated.

In case of these derivatives of compounds of the formula (III), their hydrochloric acid, p-toluenesulfonic acid, naphthalene sulfonic acid or tetralin sulfonic acid salts may also be used.

The reaction between the acid represented by the formula (II) or the reactive derivative thereof and a 7-α-amino-acylamidocephalosporin represented by the formula (III) or the derivative thereof can be carried out at any temperature and usually below about 50° C.

Furthermore, the compounds of the formula (I) where X is S-Het of the present invention can also be prepared by reacting an N-acylamino-α-arylacetamido-cephalosporin of the formula (IV),

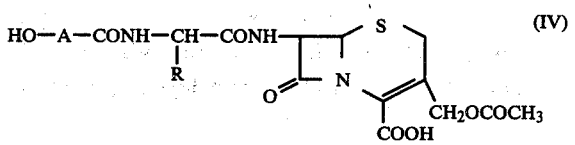

wherein A and R are each as defined above, with a thiol represented by the formula (V), HS-Het     (V)

wherein Het is as defined above.

Various well-known methods (as described in Japanese Patent Publication Nos. 12136/1971, 2340/1971, 14734/1971, Japanese Patent Application (OPI) No. 68593/1973 and *Journal of the Chemical Society*, 1965, 5015) can be applied in the preparation.

Further, another preparation of the compounds of the formula (I) is a method which comprises reacting an acylamino carboxylic acid of the formula (VI),

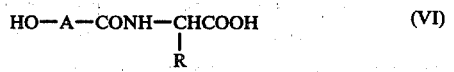

wherein A and R are each as defined above, or a reactive derivative thereof with a compound of the formula (VII),

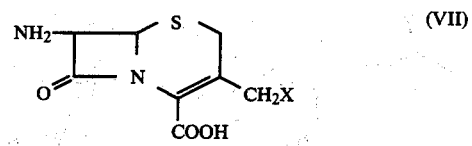

wherein X is as defined above, or a derivative thereof, and when X is an —OCOCH₃ group, further reacting the resulting reaction product, if necessary, with a heterocyclic thiol of the formula (V), HS-Het     (V)

in which Het is as defined above.

The compounds of the formula (III) can easily be prepared by the methods which are disclosed in, for example, U.S. Pat. Nos. 3,634,416 and 3,634,418, Dutch Pat. No. 70/05519, Canadian Pat. No. 873869, Japanese Patent Publication No. 14457/1971, and Japanese Pat. Application (OPI) Nos. 49983/1974, 12579/1972, 31689/1974, 54393/1974 and 49984/1974.

It has now been found that the novel cephalasporins of the formula (I) above have a strong antimicrobial activity against gram-positive as well as gram-negative bacteria with excellent pharmacokinetic properties and are useful as chemotherapeutic agents for infectious diseases of animals including human beings, poultry and cattle. The compounds of the formula (I), for instance, display noticeable antimicrobial activity against bacteria to which known cephalosporins series compounds are hardly effective such as *Pseudomonas aeraginosa*, indole positive *Proteus, Serratia* and *Enterobacter aerogeneus*. The cephalosporins of the formula (I), which characteristically have a phenyl group substituted with at least one of a ureido group, an amino group, a hydroxymethyl group or a hydroxy group represented by R, are much better distributed in serum and urine than are similar compounds without such substituents.

The compound of the general formula (I) can be administered intramuscularly or intravenously, for example, in the form of a solution, a suspension and the like.

Compositions or preparations containing the compound of the general formula (I) as an active ingredient can be prepared by admixing the compound of the formula (I) with one or more pharmaceutically acceptable carriers or diluents such as water.

A usual dosage of the compound of the formula (I) is about 400 mg to 20 g/day, preferably about 500 mg to 2 g day, in single or multiple doses, generally multiple doses, for an adult (about 60 Kg of body weight).

The following examples are intended to illustrate the preparation of compounds of the invention but are not to be construed as limiting the scope thereof. Unless otherwise indicated, all parts, percents, ratios and the like are by weight.

EXAMPLE 1

Preparation of 7-[D-α-(4-Hydroxypyridine-3-carboxyamido)-α-p-ureidophenylacetamido]cephalosporanic Acid

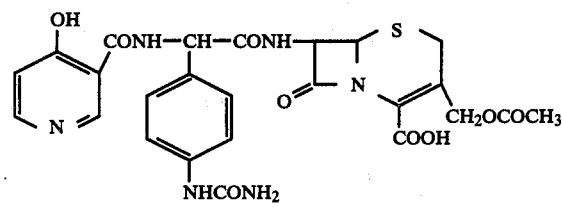

To a solution of 4.63 g of 7-(D-α-amino-p-ureidophenylacetamido)cephalosporanic acid and 2.02 g of triethylamine in 80 ml of dimethylformamide were added 2.36 g of 4-hydroxypyridine-3-carboxylic acid N-hydroxysuccinimide ester under stirring. After the mixture was reacted for 3 hours at room temperature, 1.66 g of sodium 2-ethylhexanoate was added thereto, and after 10 minutes 200 ml of dichloromethane and 100 ml of diethyl ether were further added thereto to deposit crystals. The crystals were collected by filtration and washed with diethyl ether. The product obtained was dissolved in water and the solution was adjusted to a pH of 2 under ice-cooling by adding a 3N-hydrochloric acid aqueous solution thereto with stirring. The deposited crystals were collected by filtration, washed with water and dried over phosphorus pentoxide under reduced pressure. Thus 2.6 g of the titled compound was obtained.

The free acid thus obtained was dissolved in dimethylformamide and an equimolar amount of sodium 2-ethylhexanoate and then diethyl ether were added thereto to deposit crystals. Thus the sodium salt of the titled compound was obtained.

In the same manner as described in Example 1, the following compounds were synthesized.

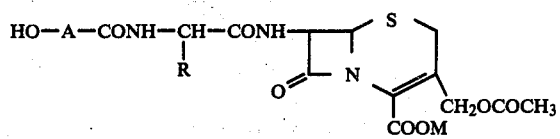

EXAMPLE 10

Preparation of 7-[D-α-(4-Hydroxy-1,5-naphthyridine-3-carboxyamido)-α-(p-ureidophenyl)acetamido]cephalosporanic Acid A solution of 4.63 g of 7-(D-α-amino-p-ureidophenylacetamido)cephalosporanic acid and 2.02 g of triethylamine in 100 ml of dichloromethane was cooled with ice and 2.45 g of 4-hydroxy-1,5-naphthyridine-3-carboxylic acid chloride hydrochloride were added thereto with stirring. After stirring for 20 minutes, 1.01 g of triethylamine and 30 ml of dimethylformamide were added and the mixture was reacted for 15 hours at the same temperature with stirring. The insoluble matter was filtered off and the filtrate was extracted with three 30 ml portions of an aqueous sodium bicarbonate solution. The aqueous extract was cooled with ice and adjusted to a pH of 2 under stirring with a 3N-hydrochloric acid aqueous solution. The deposited crystals were collected by filtration, washed with water and dried over phosphorus pentoxide under reduced pressure. Thus 2.4 g of the titled compound was obtained. The product was further converted to the sodium salt thereof using a conventional method.

EXAMPLE 11

Preparation of
7-[D-α-(4-Hydrocinnoline-3-carboxyamido)-α-(p-ureidophenylacetamido)]cephalosporanic Acid

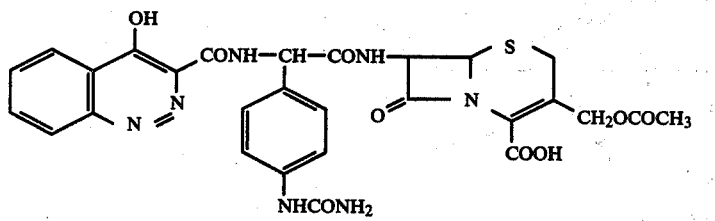

In 60 ml of dry dimethylformamide was dissolved 1.90 g of 4-hydroxycinnoline-3-carboxylic acid at room temperature (about 20°–30° C.) with stirring. To the resulting solution was added 1.78 g of carbonyldiimidazole and the mixture was stirred for 30 minutes. Thereafter, 4.63 g of 7-(D-α-amino-p-ureidophenylacetamido)cephalosporanic acid and 2.0 g of triethylamine were added thereto and the mixture was reacted for 3 hours at room temperature with stirring. To the reaction solution was added 3.64 g of a 50% sodium 2-ethylhexanoate solution in n-butanol and the mixture was stirred for 10 minutes. The reaction solution was poured into acetone and the deposited crystals were collected by filtration. The crystals were dissolved in water and the resulting solution was cooled with ice and adjusted to a pH of 2 with stirring with a 2N-hydrochloric acid aqueous solution. The deposited crystals were collected by filtration, washed with water and dried over phosphorus pentoxide under reduced pressure. Thus 3.0 g of the titled compound was obtained. The compound was converted to the sodium salt using a conventional method.

EXAMPLE 12

Preparation of
7-[D-α-(4-Hydroxypyridine-3-carboxyamido)-α-(p-ureidophenyl)acetamido]-3-(2-methyl-1,3,4-thiadiazol-5-yl) thiomethyl-3-cephem-4-carboxylic Acid To a mixture of 5.35 g of 7-(D-α-amino-p-ureidophenylacetamido)-3-(2-methyl-1,3,4-thiadiazol-5-yl)thiomethyl-3-cephem-4-carboxylic acid, 2.02 g of triethylamine and 80 ml of dimethylformamide was added 2.36 g of 4-hydroxypyridine-3-carboxylic acid N-hydroxysuccinimide ester. After the mixture was reacted for 3 hours at room temperature with stirring, 1.66 g of sodium 2-ethylhexanoate was added thereto and after 10 minutes 200 ml of acetone and 100 ml of diethyl ether were further added thereto to deposit crystals. The crystals were collected by filtration, washed with diethyl ether and dissolved in water. The resulting solution was adjusted to a pH of 2 under ice-cooling with a 2N-hydrochloric acid aqueous solution. The deposited crystals were collected by filtration, washed with water and dried over phosphorus pentoxide under reduced pressure. Thus 3.2 g of the titled compound was obtained. The compound was further converted to the sodium salt using a conventional method.

EXAMPLE 13

Preparation of
7-[D-α-(4-Hydroxypyridine-3-carboxyamido)-α-(p-ureidophenyl)acetamido]-3-(1-methyltetrazol-5-yl)thiomethyl-3-cephem-4-carboxylic Acid In the same manner as described in Example 12, the titled compound was obtained using 7-(D-α-amino-p-ureidophenylacetamido)-3-(1-methyltetrazol-5-yl)thiomethyl-3-cephem-4-carboxylic acid.

In the same manner, the following compounds were synthesized.

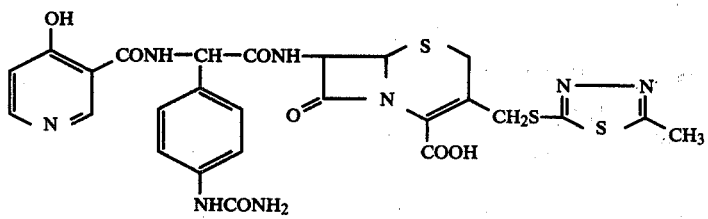

| Example No. | HO—A— | R— | —Het | M |
|---|---|---|---|---|
| 14 | 4-hydroxy-3-methylpyridinyl | p-ureidophenyl | 2-methyl-1,3,4-thiadiazol-5-yl | Na |

-continued $$HO-A-CONH-CH(R)-CONH-\text{[β-lactam]}-CH_2S-Het$$
$$COOM$$

| Example No. | HO—A— | R— | —Het | M |
|---|---|---|---|---|
| 15 | 3-hydroxy-4-methylpyridazin-yl | 3-(NHCONH$_2$)phenyl | 5-methyl-1,3,4-thiadiazol-2-yl | Na |
| 16 | 3-hydroxy-4-methylpyridazin-yl | 4-(NHCONH$_2$)phenyl | 5-methyl-1,3,4-thiadiazol-2-yl | Na |
| 17 | 3-hydroxy-4-methylpyridazin-yl | 4-(NHCONH$_2$)phenyl | 1-methyl-1H-tetrazol-5-yl | Na |
| 18 | 3-hydroxy-4-methylpyridazin-yl | 4-(NHCONH$_2$)phenyl | 1H-1,2,3-triazol-4-yl | Na |
| 19 | 4-hydroxy-5-methylpyrimidin-yl | 4-(NHCONH$_2$)phenyl | 1,3,4-thiadiazol-2-yl | Na |
| 20 | 4-hydroxy-3-methyl-1,8-naphthyridin-yl | 4-(NHCONH$_2$)phenyl | 5-methyl-1,3,4-thiadiazol-2-yl | Na |
| 21 | 4-hydroxy-3-methyl-1,8-naphthyridin-yl | 4-(NHCONH$_2$)phenyl | 1,3,4-thiadiazol-2-yl | Na |
| 22 | 4-hydroxy-3-methyl-1,8-naphthyridin-yl | 4-(NHCONH$_2$)phenyl | 1-methyl-1H-tetrazol-5-yl | Na |
| 23 | 4-hydroxy-3-methyl-1,8-naphthyridin-yl | 4-(NHCONH$_2$)phenyl | 1H-1,2,3-triazol-4-yl | Na |
| 24 | 4-hydroxy-3-methyl-1,8-naphthyridin-yl | 4-(NHCONH$_2$)phenyl | 5-mercapto-1,3,4-thiadiazol-2-yl | Na |
| 25 | 4-hydroxy-3-methyl-7-methyl-1,8-naphthyridin-yl | 4-(NHCONH$_2$)phenyl | 5-methyl-1,3,4-thiadiazol-2-yl | Na |

-continued

| Example No. | HO—A— | R— | —Het | M |
|---|---|---|---|---|
| 26 | 7-hydroxy-2-methyl-1,8-naphthyridine with CH3 | p-NHCONH2 phenyl | 1-methyl-tetrazol-5-yl | Na |
| 27 | 2-(dimethylamino)-7-hydroxy-6-methyl-1,8-naphthyridine | p-NHCONH2 phenyl | 1H-1,2,3-triazol-4-yl | Na |
| 28 | 2-(dimethylamino)-7-hydroxy-6-methyl-1,8-naphthyridine | p-NHCONH2 phenyl | 5-methyl-1,3,4-thiadiazol-2-yl | Na |
| 29 | 2-(dimethylamino)-7-hydroxy-1,8-naphthyridine | p-NHCONH2 phenyl | 1-methyl-1,2,3-triazol-4-yl | Na |

EXAMPLE 30

Preparation of 7-[D-α-(4-Hydroxypyridine-3-carboxyamido)-α-(p-ureidophenyl)acetamido]-3-(1,3,4-thiadiazol-5-yl)thiomethyl-3-cephem-4-carboxylic acid

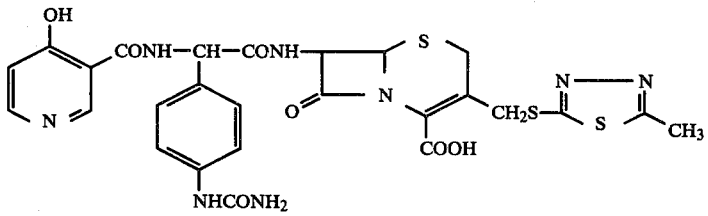

A mixture of 1.21 g of sodium 7-[D-α-(4-hydroxypyridine-3-carboxyamido)-α-(p-ureidophenyl)acetamido]cephalosporanate, 0.20 g of sodium bicarbonate, 0.36 g of 2-methyl-5-mercapto-1,3,4-thiadiazole and 25 ml of a phosphate buffer (0.1N KH2PO4-0.1N NaHPO4; 2:1 by volume; pH:6.3) was stirred for 6 hours at 60° C. Then the solution was cooled with ice and made acidic to a pH of 2 with a 3N-hydrochloric acid aqueous solution. The deposited crystals were collected by filtration, washed with water and dried over phosphorus pentoxide under reduced pressure. Thus 0.62 g of the titled compound was obtained. The compound was further converted into the sodium salt using a conventional method.

The compounds obtained in Examples 15, 16, 20, 22 and 26 were also obtained in the same manner as described in Example 30.

The following compounds were obtained in the same manner as described in Examples 1 to 12.

| Example No. | HO—A— | R |
|---|---|---|
| 31 | 2-methoxy-7-hydroxy-6-methyl-pyrido-pyrazine | m-NHCONH2 phenyl |

| | | |
|---|---|---|
| 32 | 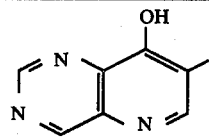 | 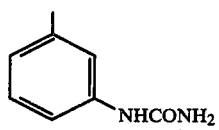 |
| 33 | 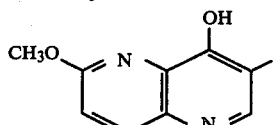 | 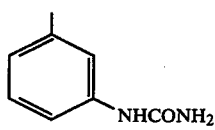 |
| 34 | 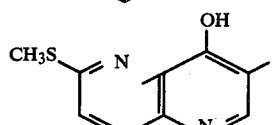 | 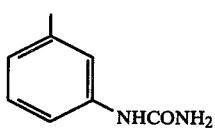 |
| 35 | 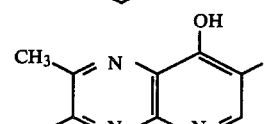 | 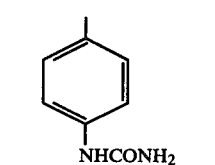 |
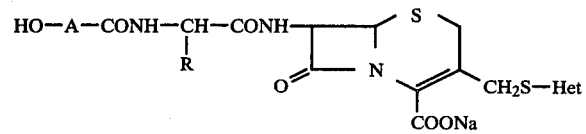
| Example No. | HO—A— | R | —Het |
|---|---|---|---|
| 36 | 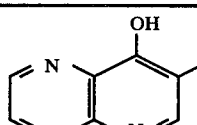 | 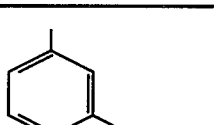 | 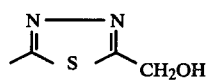 |
| 37 | 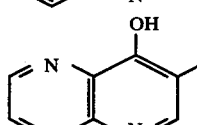 | 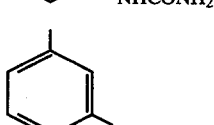 | 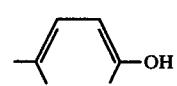 |
| 38 | 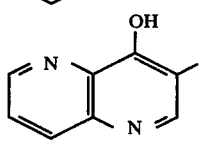 | 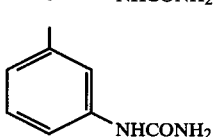 | 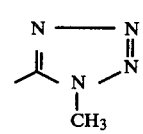 |
| 39 | 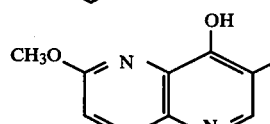 | 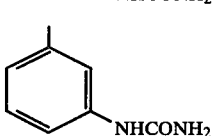 | 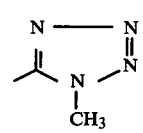 |
| 40 | 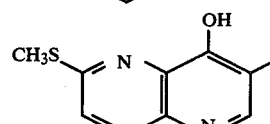 | 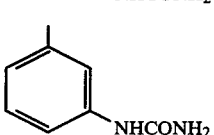 | 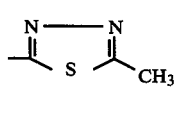 |
| 41 | 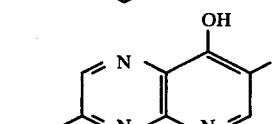 | 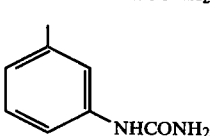 | 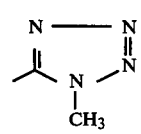 |
| 42 | 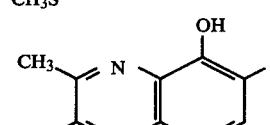 | 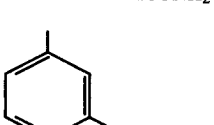 | 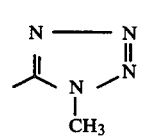 |

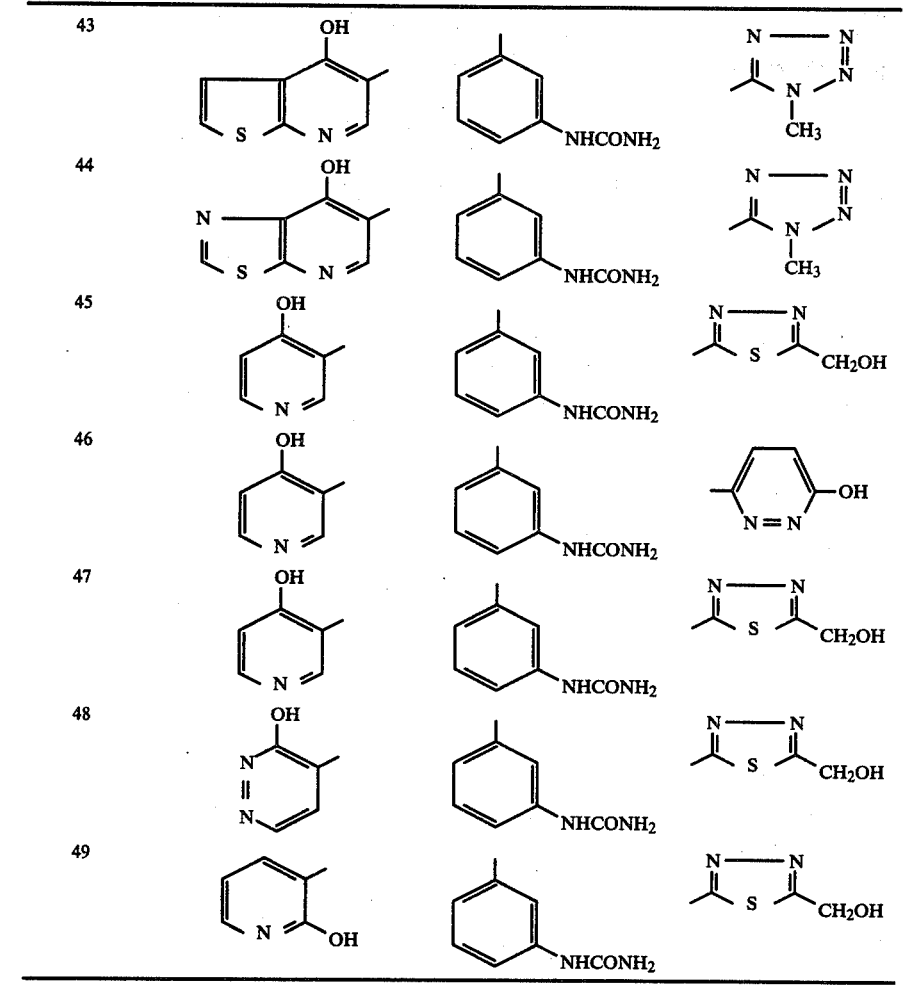

EXAMPLE 50

Preparation of
7-[D-α-(4-Hydroxy-1,5-naphthyridine-3-carboxyamido)-α-p-aminophenylacetamido]cephalosporanic Acid

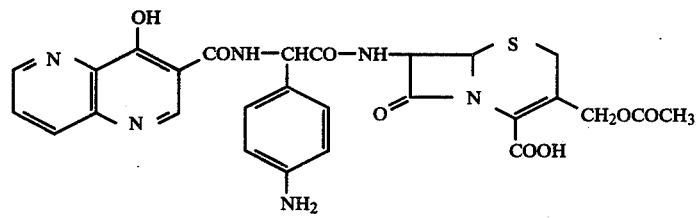

To a mixture of 4.20 g of 7-(D-α-p-aminophenylacetamido)-cephalosporanic acid, 2.02 g of triethylamine and 50 ml of dimethylformamide were added 2.87 g of 4-hydroxy-1,5-naphthyridine-3-carboxylic acid N-hydroxysuccinimide ester, and the mixture was stirred for 2 hours at room temperature. The insoluble matter was filtered off and to the filtrate were added 100 ml of dichloromethane and 300 ml of diethyl ether. The deposited crystals were collected by filtration, washed with diethyl ether and dried over phosphorus pentoxide under reduced pressure. Thus 4.7 g of the triethylamine salt of the titled compound was obtained.

The compound was dissolved in dimethylformamide and to the resulting solution was added sodium 2-ethylhexanoate in an amount of 1.1 molar times the titled compound. On further adding acetone to the solution, the sodium salt of the titled compound separated as crystals.

EXAMPLE 51

Preparation of
7-[D-α-(4-Hydroxypyridine-3-carbonamide)-α-m-aminophenylacetamido]cephalosporanic acid

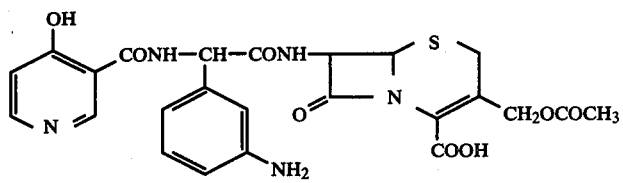

To a mixture of 4.20 g of 7-[D-α-m-aminophenylacetamido]-cephalosporanic acid, 2.02 g of triethylamine and 50 ml of dimethylformamide was added 2.36 g of 4-hydroxypyridine-3-carboxylic acid N-hydroxysuccinimide ester, and the mixture was stirred for 2 hours at room temperature.

Then 1.66 g of sodium 2-ethylhexanoate was added and, after 10 minutes, 100 ml of dichloromethane and 200 ml of diethyl ether were further added to deposit crystals. The crystals were collected by filtration, washed with diethyl ether and dried over phosphorus pentoxide under reduced pressure. Thus 4.5 g of the sodium salt of the titled compound was obtained.

EXAMPLE 52

Preparation of
7-[D-α-(4-Hydroxy-1,5-naphthyridine-3-carbonamido)-α-p-aminophenylacetamido]-3-(2-methyl-1,3,4-thiadiazol-5-yl)thiomethyl-3-cephem-4-carboxylic acid

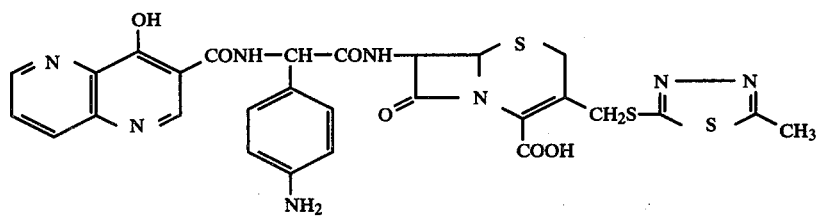

The titled compound was obtained in the same manner as described in Example 1 except that 7-(D-α-p-aminophenylacetamido)-3-(2-methyl-1,3,4-thiadiazol-5-yl)thiomethyl-3-cephem-4-carboxylic acid was used in place of 7-(D-α-p-aminophenylacetamido)cephalosporanic acid.

In the same manner as described in Examples 50 to 52, the following compounds were synthesized.

| Example No. | HO—A— | —R | X | M |
|---|---|---|---|---|
| 53 | 4-hydroxy-1,5-naphthyridin-3-yl (methyl) | m-aminophenyl | —OCOCH₃ | Na |
| 54 | 4-hydroxy-1,5-naphthyridin-3-yl | m-aminophenyl | —S-(triazoline) | Na |
| 55 | 4-hydroxy-1,5-naphthyridin-3-yl | m-aminophenyl | —S-(1-methyl-tetrazol-5-yl) | Na |
| 56 | 4-hydroxypyridin-3-yl | p-aminophenyl | —S-(2-methyl-1,3,4-thiadiazol-5-yl) | Na |

-continued

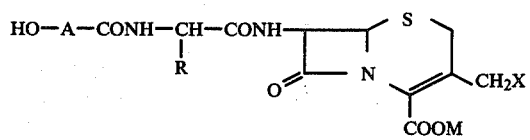

| Example No. | HO—A— | —R | X | M |
|---|---|---|---|---|
| 57 | 3-methyl-4-hydroxypyridine | 3-aminophenyl | -S-(1-methyl-tetrazol-5-yl) | Na |
| 58 | 4-methyl-3-hydroxypyridazine | 4-aminophenyl | —OCOCH₃ | Na |
| 59 | 4-methyl-3-hydroxypyridazine | 3-aminophenyl | -S-(1,3,4-thiadiazol-2-yl) | Na |
| 60 | 4-methyl-3-hydroxypyridazine | 3-aminophenyl | -S-(1-methyl-1,2,4-triazol-3-yl) | Na |
| 61 | 5-methyl-4-hydroxypyrimidine | 4-aminophenyl | -S-(5-methyl-1,3,4-thiadiazol-2-yl) | Na |
| 62 | 7-methyl-4-hydroxy-1,8-naphthyridine-3-yl | 3-aminophenyl | —OCOCH₃ | Na |
| 63 | 7-methyl-4-hydroxy-1,8-naphthyridine-3-yl | 3-aminophenyl | -S-(4-methyl-1,2,4-triazol-3-yl) | Na |

EXAMPLE 64

Preparation of 7-[D-α-(4-Hydroxy-1,5-naphthyridine-3-carbonamido)-α-m-aminophenylacetamido]-3-(1,3,4-thiadiazol-5-yl)thiomethyl-3-cephem-4-carboxylic acid

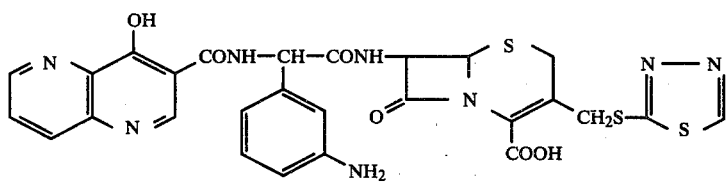

A mixture of 1.18 g of 7-[D-α-(4-hydroxy-1,5-naphthyridine-3-carbonamido)-α-m-aminophenylacetamido]-cephalosporanic acid, 0.368 g of sodium bicarbonate, 0.32 g of 2-mercapto-1,3,4-thiadiazole and 25 ml of a phosphate buffer (0.1N KH₂PO₄—0.1N NaHPO₄; 2:1 by volume; pH:6.3) was stirred for 5.5 hours at 60° C. Then 20 ml of ethanol was added and the mixture was kept at 0° to 5° C. overnight. The deposited crystals were collected by filtration, washed with ethanol and dried over silica gel under reduced pressure. Thus, 1.05 g of the sodium salt of the titled compound was obtained.

The following compounds were obtained in the same manner as described in Examples 50 to 52 and 64.

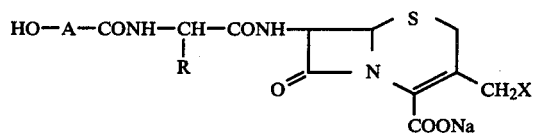

| Example No. | HO—A— | R | —X |
|---|---|---|---|
| 65 | 3-methyl-4-hydroxy-1,5-naphthyridin-2-yl | 3-aminophenyl | -S-(3-hydroxypyridazin-6-yl) |
| 66 | 3-methyl-4-hydroxy-1,5-naphthyridin-2-yl | 3-aminophenyl | -S-(5-hydroxymethyl-1,3,4-thiadiazol-2-yl) |
| 67 | 7-methoxy-3-methyl-4-hydroxy-1,5-naphthyridin-2-yl | 3-aminophenyl | -S-(1-methyl-1H-tetrazol-5-yl) |
| 68 | 3-methyl-4-hydroxy-1,5-naphthyridin-2-yl | 3-aminophenyl | -S-(1-methyl-1H-tetrazol-5-yl) |
| 69 | 3-methyl-4-hydroxypyridin-2-yl | 3-aminophenyl | -S-(5-hydroxymethyl-1,3,4-thiadiazol-2-yl) |
| 70 | 2-methylthio-6-methyl-5-hydroxypyrido[2,3-b]pyrazin-7-yl | 3-aminophenyl | -S-(1-methyl-1H-tetrazol-5-yl) |
| 71 | 3-methyl-4-hydroxy-1,5-naphthyridin-2-yl | 4-aminophenyl | -S-(1-methyl-1H-tetrazol-5-yl) |
| 72 | 2-methylthio-6-methyl-5-hydroxypyrido[2,3-d]pyrimidin-7-yl | 3-aminophenyl | -S-(1-methyl-1H-tetrazol-5-yl) |
| 73 | 2-methylthio-6-methyl-5-hydroxypyrido[2,3-d]pyrimidin-7-yl | 3-aminophenyl | -S-(4,5-dihydro-1,2,3-triazol-4-yl) |

-continued

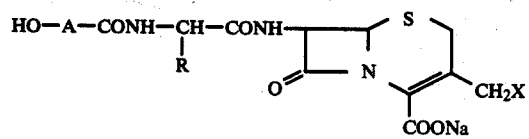

| Example No. | HO—A— | R | —X |
|---|---|---|---|
| 74 | 6-(dimethylamino)-4-hydroxy-3-methyl-1,5-naphthyridinyl | 3-aminophenyl | 1-methyltetrazol-5-ylthio |
| 75 | 4-hydroxy-3-methylthieno[2,3-b]pyridinyl | 3-aminophenyl | 5-methyl-1,3,4-thiadiazol-2-ylthio |
| 76 | 4,8-dihydroxy-3-methyl-1,5-naphthyridinyl | 3-aminophenyl | 5-methyl-1,3,4-thiadiazol-2-ylthio |
| 77 | 6-hydroxy-4-hydroxy-3-methyl-1,5-naphthyridinyl | 3-aminophenyl | 1-methyltetrazol-5-ylthio |
| 78 | 4-hydroxy-3-methyl-1,5-naphthyridinyl | 3-aminophenyl | 5-(methylamino)-1,3,4-thiadiazol-2-ylthio |
| 79 | 4-hydroxy-3-methyl-1,5-naphthyridinyl | 3-aminophenyl | 5-(aminomethyl)-1,3,4-thiadiazol-2-ylthio |
| 80 | 4-hydroxy-3-methyl-1,5-naphthyridinyl | 3-aminophenyl | 5-oxo-1,3,4-thiadiazol-2-ylthio |
| 81 | 4-hydroxy-3-methyl-1,5-naphthyridinyl | 4-aminophenyl | 5-(hydroxymethyl)-1,3,4-thiadiazol-2-ylthio |
| 82 | 4-hydroxy-3-methyl-1,5-naphthyridinyl | 4-aminophenyl | 1-methyltetrazol-5-ylthio |

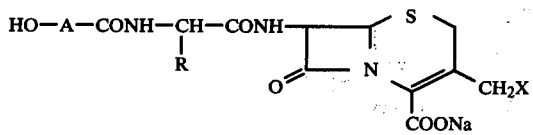

| Example No. | HO—A— | R | —X |
|---|---|---|---|
| 83 | 4-hydroxy-3-methylpyridine | 4-aminophenyl | -S-[thiadiazole]-CH₂OH |
| 84 | 4-hydroxy-3-methylpyridine | 3-aminophenyl | -S-[thiadiazole]-CH₂OH |
| 85 | 4-hydroxy-3-methylpyridine | 3-aminophenyl | -S-[pyridazine]-OH |
| 86 | 3-hydroxy-4-methylpyridazine | 3-aminophenyl | -S-[thiadiazole]-CH₂OH |
| 87 | 3-hydroxy-4-methylpyridazine | 3-aminophenyl | -S-[pyridazine]-OH |

EXAMPLE 88

Preparation of 7-[DL-α-(4-Hydroxypyridine-3-carbonamido)-α-p-hydroxymethylphenylacetamido]cephalosporanic Acid

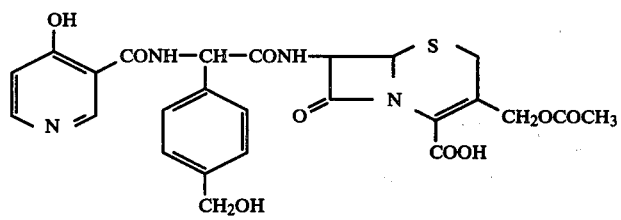

To a solution of 4.35 g of 7-[DL-α-p-hydroxymethylphenylacetamido]cephalosporanic acid and 2.02 g of triethylamine in 80ml of dichloromethane were added under ice-cooling 2.36 g of 4-hydroxypyridine-3-carboxylic acid N-hydroxysuccinimide ester and 40 ml of dimethylformamide with stirring, and the mixture was stirred for 30 minutes at the same temperature. After the mixture was further reacted for 2 hours at room temperature with stirring, 1.66 g of sodium 2-ethylhexanoate was added, and, after 10 minutes, 100 ml of dichloromethane and 200 ml of diethyl ether were further added thereto to deposit crystals. The crystals were collected by filtration, washed with diethyl ether and dried over phosphorus pentoxide under reduced pressure. Thus 4.0 g of the sodium salt of the titled compound was obtained.

EXAMPLE 89

Preparation of
7-[DL-α-(4-Hydroxy-1,5-naphthyridine-3-carbonamido)-α-p-hydroxymethylphenylacetamido]cephalosporanic Acid

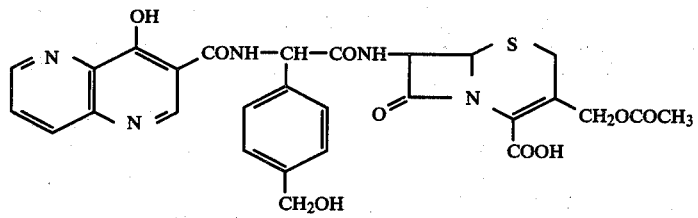

To a solution of 4.35 g of 7-[DL-α-p-hydroxymethylphenylacetamido]cephalosporanic acid and 2.02 g of triethylamine in 60 ml of dimethylformamide were added 2.87 g of 4-hydroxy-1,5-naphthyridine-3-carboxylic acid N-hydroxysuccinimide ester, and the mixture was stirred for 2 hours at room temperature. The insoluble matter was filtered off and 100 ml of dichloromethane and 350 ml of diethyl ether were added to the filtrate to deposit crystals. The crystals were collected by filtration, washed with diethyl ether and dried over phosphorus pentoxide under reduced pressure. Thus 4.2 g of the triethylamine salt of the titled compound was obtained.

The compound was converted to the sodium salt using a conventional method.

EXAMPLE 90

Preparation of
7-[DL-α-(4-Hydroxypyridine-3-carbonamido)-α-p-hydroxymethylphenylacetamido]-3-(2-methyl-1,3,4-thiadiazol-5-yl)thiomethyl-3-cephem-4-carboxylic Acid

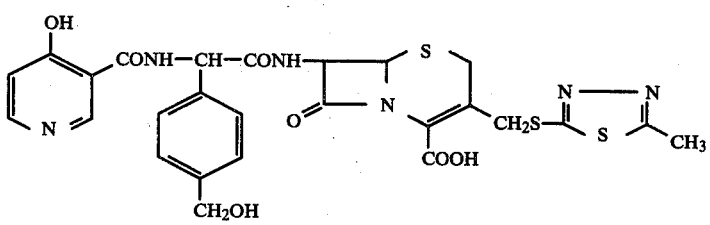

To a solution of 5.07 g of 7-(DL-α-p-hydroxymethylphenylacetamido)-3-(2-methyl-1,3,4-thiadiazol-5-yl)thiomethyl-3-cephem-4-carboxylic acid and 2.02 g of triethylamine in 80 ml of dimethylformamide were added 2.36 g of 4-hydroxypyridine-3-carboxylic acid N-hydroxysuccinimide ester with stirring, and the mixture was reacted for 2 hours at room temperature with stirring. Then 1.66 g of sodium 2-ethylhexanoate was added and, after 10 minutes, 200 ml of acetone and 100 ml of diethyl ether were further added thereto to deposit crystals. The crystals were collected by filtration, washed with diethyl ether and dried over phosphorus pentoxide under reduced pressure. Thus 4.8 g of the sodium salt of the titled compound was obtained.

In the same manner as described in Examples 88 to 90, the following compounds were synthesized.

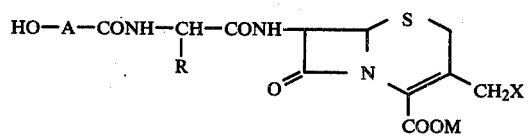

| Example No. | HO—A— | —R | X | M |
|---|---|---|---|---|
| 91 | 4-hydroxypyridin-3-yl | p-CH₂OH-phenyl | -S-(1-methyl-1H-tetrazol-5-yl) | Na |
| 92 | 3-hydroxypyridazin-4-yl | p-CH₂OH-phenyl | —OCOCH₃ | Na |

-continued

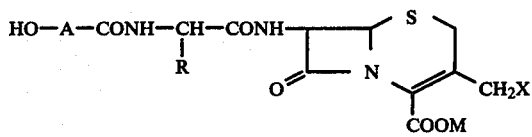

| Example No. | HO—A— | —R | X | M |
|---|---|---|---|---|
| 93 | 3-hydroxy-4-methylpyridazine | p-(CH₂OH)phenyl | —S-(5-methyl-1,3,4-thiadiazol-2-yl) | Na |
| 94 | 4-hydroxy-5-methylpyrimidine | p-(CH₂OH)phenyl | —S-(1-methyl-1H-tetrazol-5-yl) | |
| 95 | 4-hydroxy-5-methylpyrimidine | p-(CH₂OH)phenyl | —S-(1,3,4-thiadiazol-2-yl) | Na |
| 96 | 4-hydroxy-3-methyl-1,5-naphthyridine | p-(CH₂OH)phenyl | —S-(5-methyl-1,3,4-thiadiazol-2-yl) | Na |
| 97 | 4-hydroxy-3-methyl-1,5-naphthyridine | p-(CH₂OH)phenyl | —S-(1-methyl-1H-tetrazol-5-yl) | Na |
| 98 | 4-hydroxy-3-methyl-1,5-naphthyridine | p-(CH₂OH)phenyl | —S-(1H-1,2,3-triazol-4-yl) | Na |
| 99 | 4-hydroxy-3-methyl-7-methyl-1,8-naphthyridine | p-(CH₂OH)phenyl | —OCOCH₃ | Na |
| 100 | 4-hydroxy-3-methyl-7-methyl-1,8-naphthyridine | p-(CH₂OH)phenyl | —S-(5-methyl-1,3,4-thiadiazol-2-yl) | Na |

EXAMPLE 101

Preparation of 7-[DL-α-(4-Hydroxy-1,5-naphthyridine-3-carbonamido)-α-p-hydroxymethylphenylacetamido]-3-(2-methyl-1,3,4-thiadiazol-5-yl)thiomethyl-3-cephem-4-carboxylic Acid

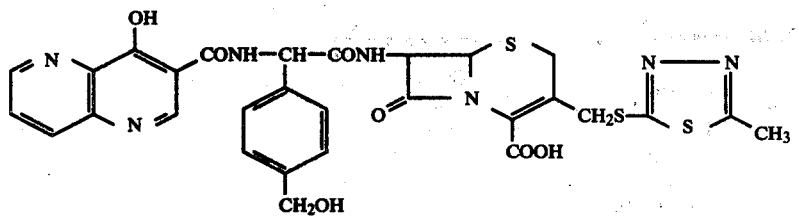

A mixture of 3.03 g of 7-[DL-α-(4-hydroxy-1,5-naphthyridine-3-carbonamido)-α-p-hydroxymethylphenylacetamido]cephalosporanic acid, 0.92 g of sodium bicarbonate, 0.90 g of 2-methyl-5-mercapto-1,3,4-thiadiazole and 60 ml of a phosphate buffer (0.1 N $KH_2PO_4$—0.1 N $NaHPO_4$; 2:1 by volume; pH 6.3) was stirred for 5.5 hours at 50° to 60° C. Then 40 ml of ethanol was added thereto and the mixture was kept at 0° to 5° C. overnight. The deposited crystals were collected by filtration, washed with ethanol and dried over phosphorus pentoxide under reduced pressure. Thus 2.5 g of the sodium salt of the titled compound was obtained.

The compounds obtained in Examples 91, 94 and 98 were obtained in the same manner as described in Example 101.

The following compounds were obtained in the same manner as described in Examples 88 to 90.

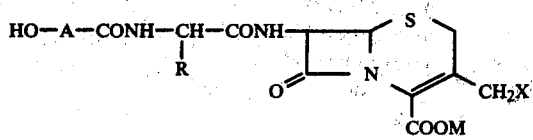

EXAMPLE 113

Preparation of
7-[D-α-(4-Hydroxypyridine-3-carbonamido)-α-p-hydroxyphenylacetamido]cephalosporanic Acid

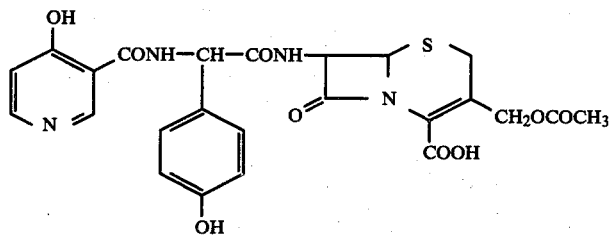

To a mixture of 4.21 g of 7-[D-α-p-hydroxyphenylacetamido]cephalosporanic acid, 60 ml of dichloromethane and 2.02 g of triethylamine were added under ice-cooling 2.36 g of 4-hydroxypyridine-3-carboxylic acid N-hydroxysuccinimide ester and 30 ml of dimethylformamide with stirring, and the mixture was stirred for 30 minutes at the same temperature. After the mixture was further reacted for 2 hours at room temperature with stirring, 1.66 g of sodium 2-ethylhexanoate was added and, after 10 minutes, 200 ml of dichloromethane and 100 ml of diethyl ether were further added thereto to deposit crystals. The crystals were collected by filtration, and washed with diethyl ether. The crystals were dissolved in water and the resulting solution was cooled with ice and made acidic to a pH of 2 under stirring with a 3N-hydrochloric acid aqueous solution.

The deposited crystals were collected by filtration, washed with water and dried over phosphorus pentoxide under reduced pressure. Thus 2.1 g of the titled compound was obtained. The free acid thus obtained was added to 13 ml of dimethylformamide and 1.1 molar equivalents of sodium 2-ethylhexanoate was added thereto. On further adding dichloromethane and acetone to deposit crystals, 1.9 g of the sodium salt of the titled compound was obtained as crystals.

The following compounds were obtained in the same manner as described in Example 113.

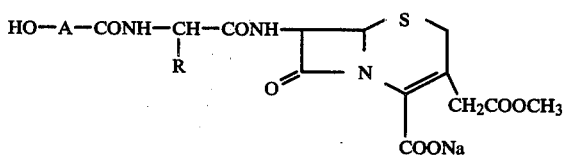

| Example No. | HO—A— | R— |
|---|---|---|
| 114 | 4-hydroxy-3-pyridyl (OH at 4, attached at 3) | 3-hydroxyphenyl |
| 115 | 2-hydroxy-3-pyridyl | 4-hydroxyphenyl |
| 116 | 2-hydroxy-pyrimidin-5-yl (OH, N=N) | 4-hydroxyphenyl |
| 117 | 4-hydroxy-3-pyridyl | 2-chloro-4-hydroxyphenyl (HO, Cl) |
| 118 | 2-hydroxy-4-hydroxypyrimidinyl (HO, N, N, OH) | 4-hydroxyphenyl |

-continued

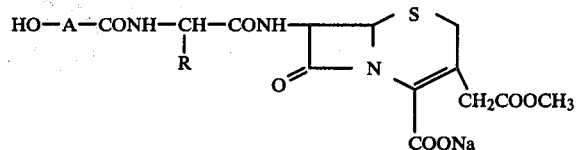

| Example No. | HO—A— | R— |
|---|---|---|
| 119 | (4-hydroxy-pyrimidine with OH, CH3) | (4-hydroxyphenyl) |

EXAMPLE 120

Preparation of
7-[D-α-(4-Hydroxy-1,5-naphthyridine-3-carbonamido)-α-p-hydroxyphenylacetamido]cephalosporanic Acid

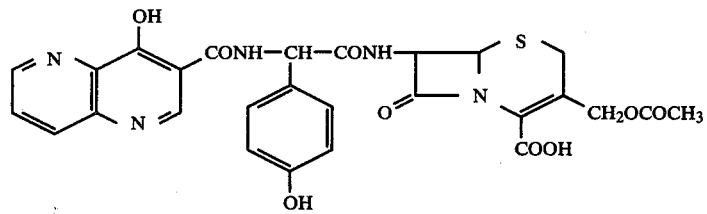

To a solution of 4.21 g of 7-[D-α-p-hydroxyphenylacetamido]cephalosporanic acid and 1.975 g of triethylamine in 80 ml of dimethylformamide were added 2.87 g of 4-hydroxy-1,5-naphthyridine-3-carboxylic acid N-hydroxysuccinimide ester, and the mixture was stirred for 2 hours at room temperature. The insoluble matter was filtered off and to the filtrate were added 80 ml of dichloromethane and 350 ml of diethyl ether. The deposited crystals were collected by filtration, washed with diethyl ether and dried over phosphorus pentoxide under reduced pressure. Thus 4.4 g of the triethylamine salt of the titled compound was obtained. The compound was converted to the sodium salt using a conventional method.

EXAMPLE 121

Preparation of
7-[D-α-(4-Hydroxy-1,5-naphthyridine-3-carbonamido)-α-p-hydroxyphenylacetamido]cephalosporanic Acid To an ice-cooled solution of 4.21 g of 7-[D-α-p-hydroxyphenylacetamido]cephalosporanic acid and 2.02 g of triethylamine in 100 ml of dichloromethane was added 2.45 g of 4-hydroxy-1,5-naphthyridine-3-carboxylic acid chloride hydrochloride with stirring, and the mixture was stirred for 20 minutes. Thereafter 1.01 g of triethylamine was added and the mixture was reacted for 3 hours at the same temperature. The insoluble matter was filtered off and the filtrate was extracted with three 20 ml portions of an aqueous sodium bicarbonate solution. The aqueous extract was cooled with ice and made acidic to a pH of 2 with a 1N-hydrochloric acid aqueous solution under stirring. The deposited crystals were collected by filtration, washed with water, methanol, and then diethyl ether and dried over phosphorus pentoxide under reduced pressure. Thus 2.2 g of the titled compound was obtained. The compound was converted to the sodium salt using sodium 2-ethylhexanoate.

The following compounds were synthesized in the same manner as described in Example 120.

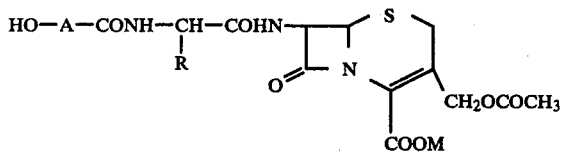

| Example No. | HO—A— | R— | M |
|---|---|---|---|
| 122 | (4-hydroxy-1,5-naphthyridinyl with CH3) | (2-Cl-4-OH-phenyl with CH3) | Na |
| 123 | (4-hydroxy-1,8-naphthyridinyl with CH3, CH3) | (4-OH-phenyl with CH3) | Na |

EXAMPLE 124

Preparation of
7-[D-α-(4-hydroxycinnoline-3-carbonamido)-α-p-hydroxyphenylacetamido]cephalosporanic acid

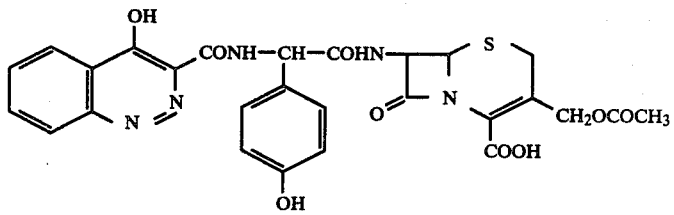

In 60 ml of dry dimethylformamide was dissolved 1.90 g of 4-hydroxycinnoline-3-carboxylic acid at room temperature with stirring, and 1.78 g of carbonyldiimidazole was added thereto followed by stirring for 30 minutes. Then 4.21 g of 7-[D-α-p-hydroxyphenylacetamido]cephalosporanic acid and 1.8 g of triethylamine were added thereto and the mixture was stirred for 3 hours at room temperature. Thereafter 3.64 g of a 50% sodium 2-ethylhexanoate solution in n-butanol were added followed by stirring for 10 minutes. The reaction solution was poured into acetone and the deposited crystals were collected by filtration. The crystals were dissolved in water and the resulting solution was cooled with ice and adjusted to a pH of 2 with a 1N-hydrochloric acid aqueous solution with stirring. The deposited crystals were collected by filtration and dried over phosphorus pentoxide under reduced pressure. Thus 3.2 g of the titled compound was obtained. The compound was converted to the sodium salt using sodium 2-ethylhexanoate.

EXAMPLE 125

Preparation of
7-[D-α-(4-Hydroxypyridine-3-carbonamido)-α-p-hydroxyphenylacetamido]-3-(2-methyl-1,3,4-thiadiazol-5-yl)thiomethyl-3-cephem-4-carboxylic Acid.

at room temperature with stirring, 1.66 g of sodium 2-ethylhexanoate was added and, after 10 minutes, 200 ml of acetone and 100 ml of diethyl ether were further added thereto to deposit crystals. The crystals were collected by filtration and washed with diethyl ether.

The crystals were dissolved in water and the resulting solution were cooled with ice and made acidic to a pH of 2 with a 2N-hydrochloric acid aqueous solution. The deposited crystals were collected by filtration, washed with water and dried over phosphorus pentoxide under reduced pressure. Thus 2.6 g of the titled compound was obtained.

A mixture of 4.93 g of 7-(D-α-p-hydroxyphenylacetamido)-3-(2-methyl-1,3,4-thiadiazol-5-yl)thiomethyl-3-cephem-4-carboxylic acid, 2.02 g of triethylamine and 80 ml of dimethyl sulfoxide was stirred at room temperature and 2.36 g of 4-hydroxypyridine-3-carboxylic acid N-hydroxysuccinimide ester was added thereto. After the mixture was stirred for 30 minutes, 1.66 g of sodium 2-ethylhexanoate was added to the reaction solution and, after 10 minutes, 2.0 liters of acetone were further added thereto to deposit crystals. The crystals were collected by filtration, washed with acetone and diethyl ether and dried over phosphorus pentoxide under reduced pressure. Thus 5.2 g of the sodium salt of the titled compound was obtained.

EXAMPLE 126

Preparation of
7-[D-α-(4-Hydroxypyridine-3-carbonamido)-α-p-hydroxyphenylacetamido]-3-(1-methyltetrazol-5-yl)thi-

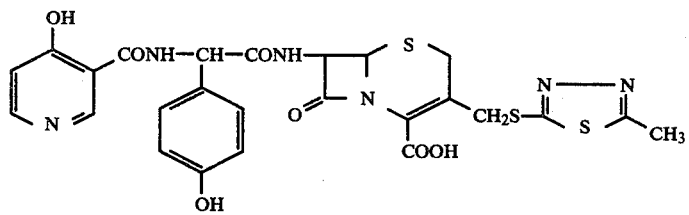

To a mixture of 4.93 g of 7-(D-α-p-hydroxyphenylacetamido)-3-(2-methyl-1,3,4-thiadiazol-5-yl)thiomethyl-3-cephem-4-carboxylic acid, 2.02 g of triethylamine and 80 ml of dimethylformaide was added under ice-cooling 2.36 g of 4-hydroxypyridine-3-carboxylic acid N-hydroxysuccinimide ester with stirring, and the mixture was stirred for 30 minutes at the same temperature. After the mixture was further reacted for 2 hours omethyl-3-cephem-4-carboxylic acid In the same manner as described in Example 125, the titled compound was obtained using 7-(D-α-p-hydroxyphenylacetamido)-3-(1-methyltetrazol-5-yl)thiomethyl-3-cephem-4-carboxylic acid.

In the same manner, the following compounds were obtained.

$$\text{HO-A-CONH-CHCOHN-}\underset{R}{\overset{\phantom{x}}{|}}\text{[β-lactam-cephem]-CH}_2\text{S-Het}$$

| Example No. | HO—A— | R— | —Het | M |
|---|---|---|---|---|
| 127 | 3-hydroxy-4-methylpyridazin-yl | 4-hydroxyphenyl | 2-methyl-1,3,4-thiadiazol-5-yl | Na |
| 128 | 3-hydroxy-4-methylpyridazin-yl | 4-hydroxyphenyl | 1-methyl-1H-tetrazol-5-yl | Na |
| 129 | 4-hydroxy-3-methyl-1,5-naphthyridin-yl | 4-hydroxyphenyl | 2-methyl-1,3,4-thiadiazol-5-yl | Na |
| 130 | 4-hydroxy-3-methyl-1,5-naphthyridin-yl | 4-hydroxyphenyl | 1,3,4-thiadiazol-2-yl | Na |
| 131 | 4-hydroxy-3-methyl-1,5-naphthyridin-yl | 4-hydroxyphenyl | 1-methyl-1H-tetrazol-5-yl | Na |
| 132 | 4-hydroxy-3-methyl-1,5-naphthyridin-yl | 3-chloro-4-hydroxyphenyl | 1-methyl-1H-tetrazol-5-yl | Na |
| 133 | 4-hydroxy-3-methyl-1,5-naphthyridin-yl | 4-hydroxyphenyl | 2-methyl-2H-1,2,3,4-tetrazol-5-yl | Na |
| 134 | 4-hydroxy-3-methyl-1,5-naphthyridin-yl | 4-hydroxyphenyl | 1H-1,2,3-triazol-4-yl | Na |

EXAMPLE 135

Preparation of 7-[D-α-(4-Hydroxy-1,5-naphthyridine-3-carbonamido)-α-p-hydroxyphenylacetamido]-3-(2-methyl-1,3,4-thiadiazol-5-yl)thiomethyl-3-cephem-4-carboxylic Acid

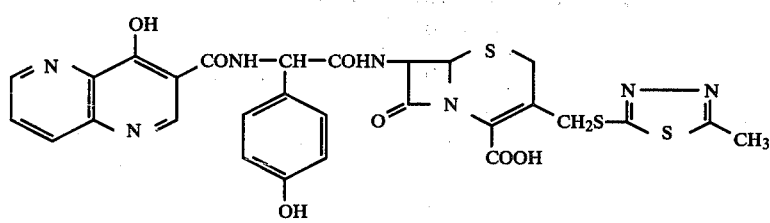

A mixture of 1.18 g of 7-[D-α-(4-hydroxy-1,5-naphthyridine-3-carbonamido)-α-p-hydroxyphenylacetamido]cephalosporanic acid, 0.368 g of sodium bicarbonate, 0.36 g of 2-methyl-5-mercapto-1,3,4-thiadiazole and 23 ml of a phosphate buffer (0.1 N KH$_2$PO$_4$-0.1 N NaHPO$_4$; 2:1 by volume; pH 6.3) was stirred for 5.5 hours at 50° C. to 60° C. Then 20 ml of ethanol were added thereto and the mixture was kept at 0° to 5° C. overnight. The deposited crystals were collected by filtration, washed with ethanol and dried over phosphorus pentoxide under reduced pressure. Thus 1.0 g of the sodium salt of the titled compound was obtained.

The compounds obtained in Examples 125, 127 and 128 were obtained in the same manner as described in Example 135.

The following compounds were synthesized in the same manner as described in Example 120.

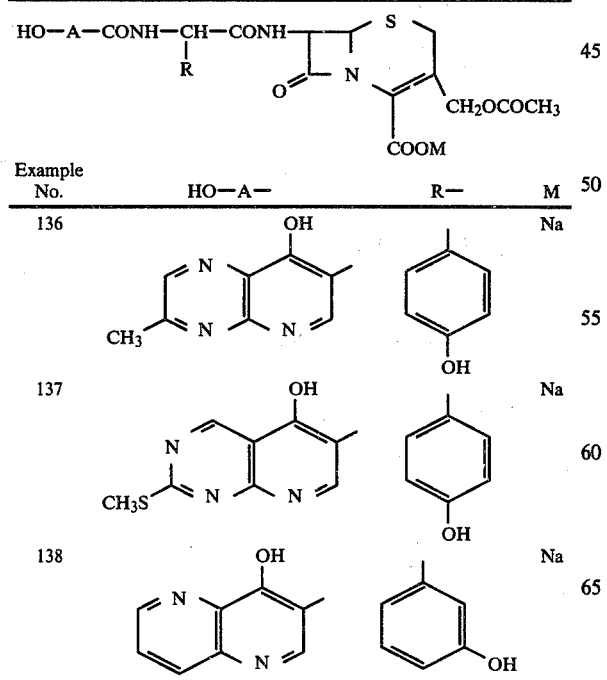

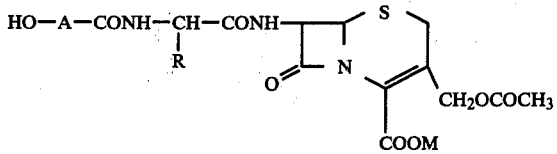

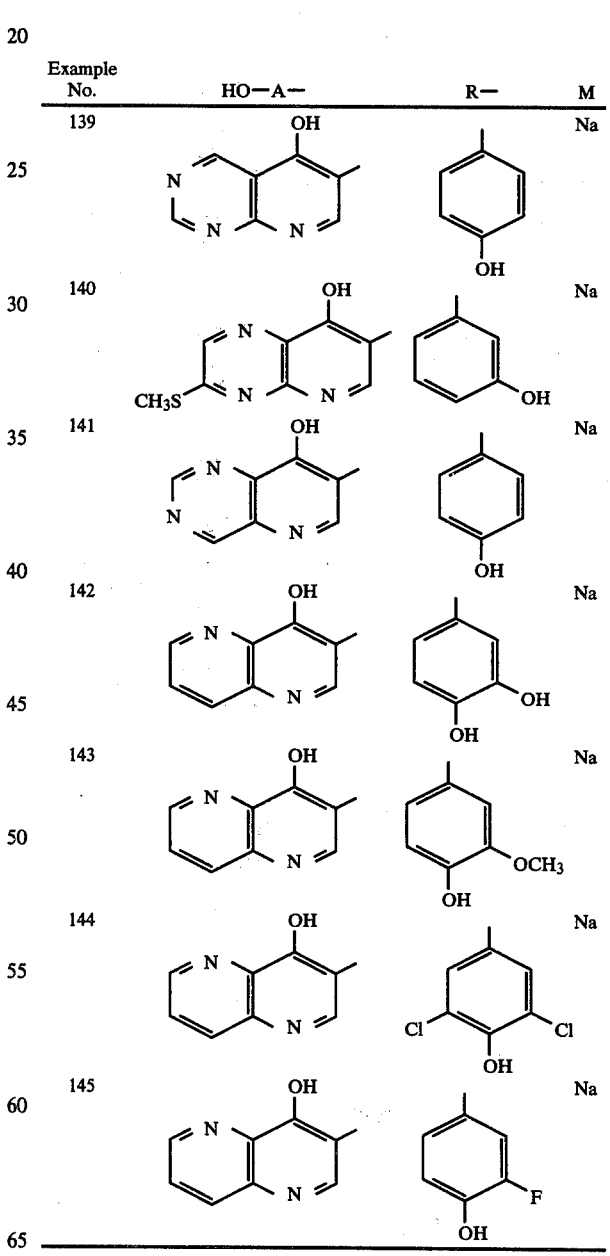

The following compounds were synthesized in the same manner as described in Example 125.

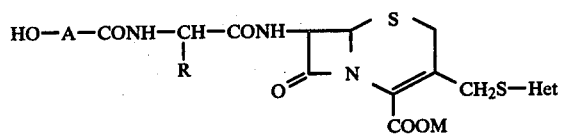
| Example No. | HO—A— | R— | —Het | M |
|---|---|---|---|---|
| 146 | | | | Na |
| 147 | | | | Na |
| 148 | | | | Na |
| 149 | | | | Na |
| 150 | | | | Na |
| 151 | | | | Na |
| 152 | | | | Na |
| 153 | | | | Na |
| 154 | | | | Na |

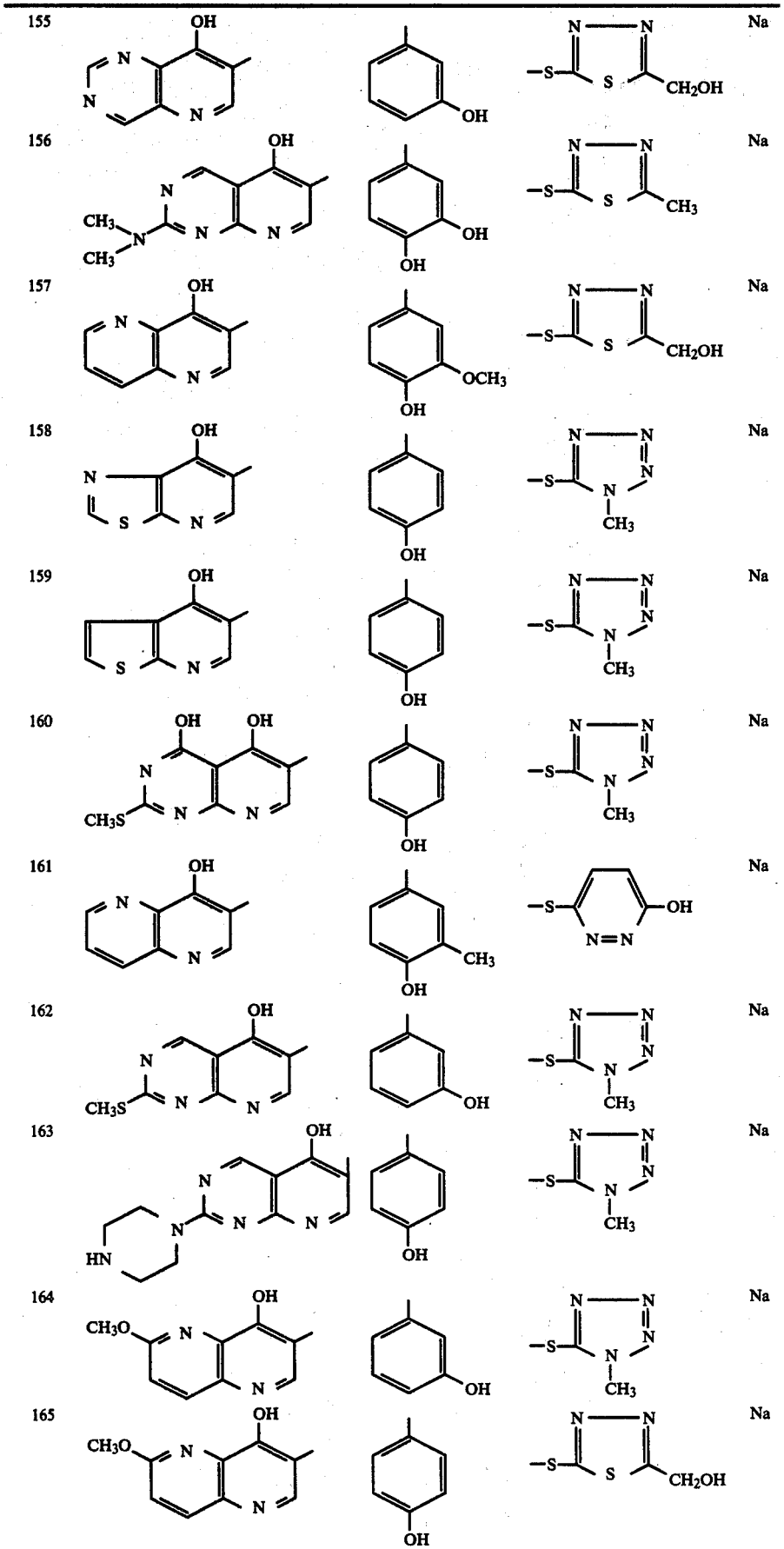

-continued
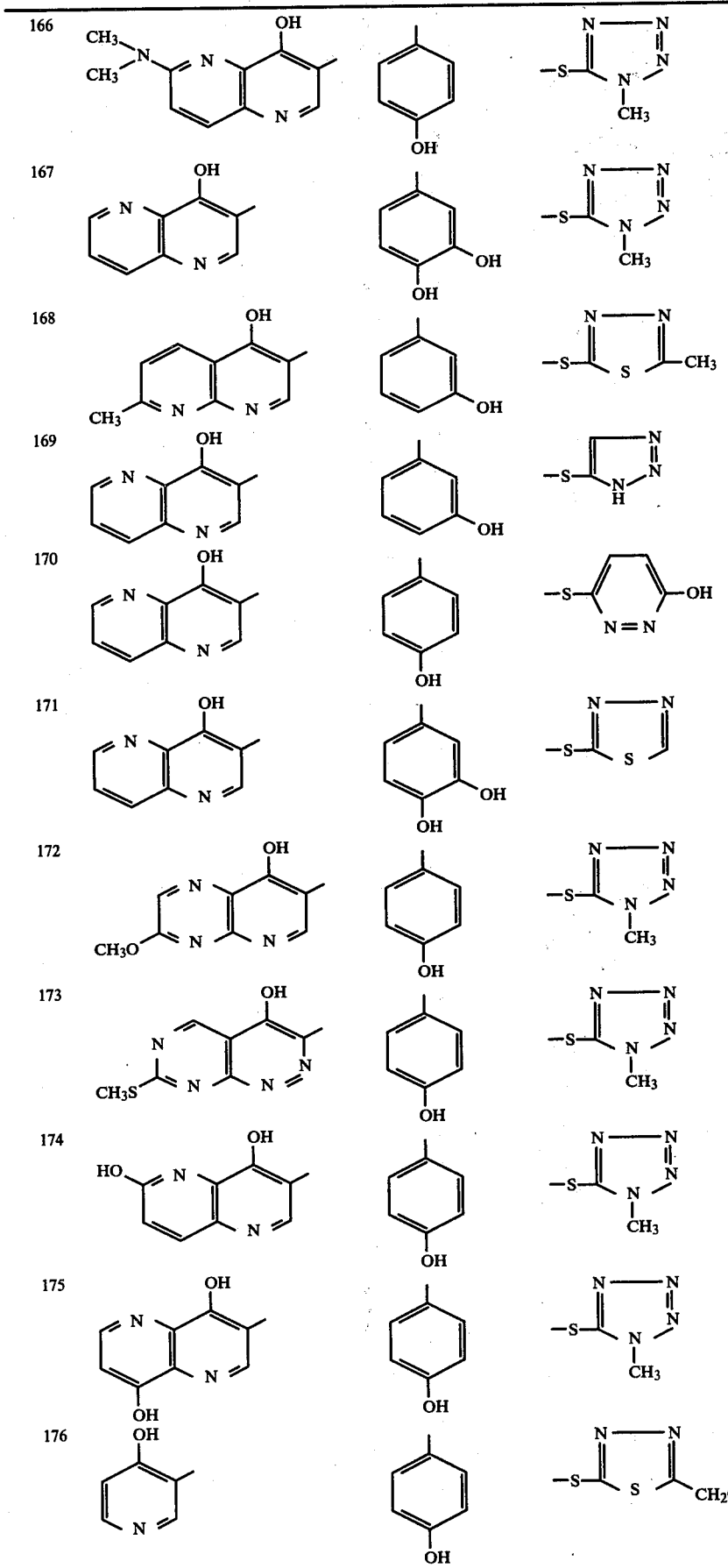

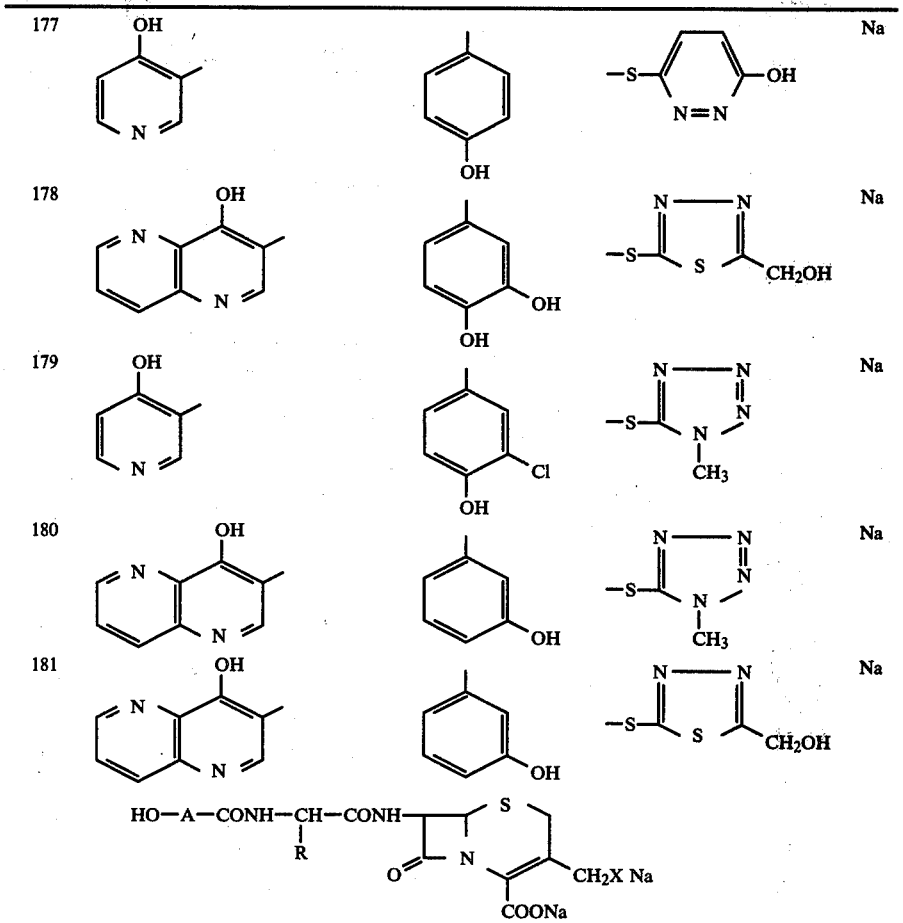
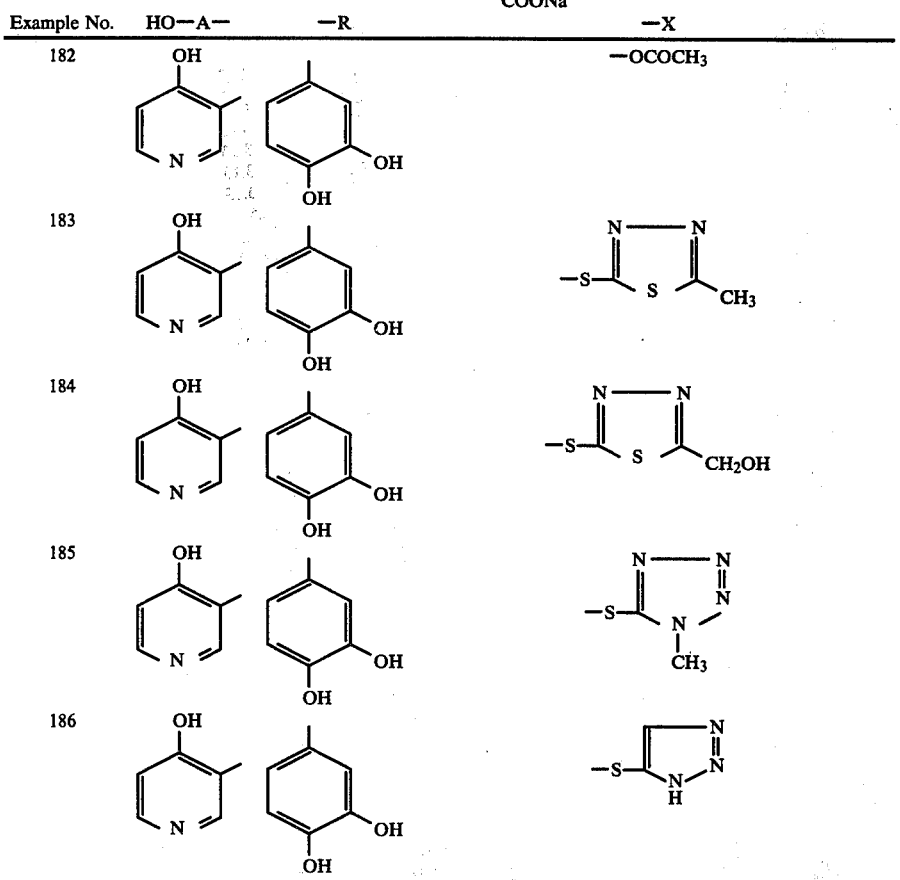

-continued

| 187 | 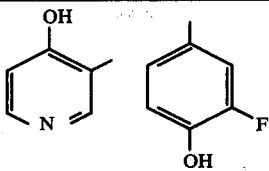 | 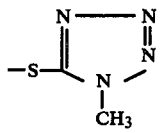 | |

Anti-microbial activity tests were carried out on the compounds obtained in the Examples. The results obtained are summarized in the following Table.

| | Minimum Inhibitory Concentration (μg/ml) | | | | | | | |
|---|---|---|---|---|---|---|---|---|
| Example No. | Staphylococcus aureus 209 P | Staphylococcus aureus* FS 289 | Escherichia coli NIHJ | Klebsiella pneumoniae 602 | Proteus vulgaris HX 19 | Pseudomonas aeruginosa 104 | Serratia No.72 | Enterobacter aerogeneus No.75 |
| 1 | 0.39 | 3.13 | 12.5 | 12.5 | 0.2 | 6.25 | >200 | 25 |
| 2 | 0.39 | 6.25 | 12.5 | 12.5 | 0.39 | 6.25 | >200 | 25 |
| 3 | 0.39 | 6.25 | 25 | 25 | 0.39 | 12.5 | >200 | 25 |
| 4 | 0.39 | 6.25 | 6.25 | 6.25 | 0.2 | 25 | 100 | 50 |
| 5 | 0.39 | 6.25 | 12.5 | 12.5 | 0.39 | 12.5 | 200 | 50 |
| 6 | 0.39 | 6.25 | 12.5 | 12.5 | 0.2 | 12.5 | 200 | 25 |
| 7 | 0.78 | 6.25 | 3.13 | 3.13 | 0.78 | 6.25 | 50 | 6.25 |
| 8 | 0.78 | 6.25 | 6.25 | 12.5 | 0.39 | 6.25 | 50 | 12.5 |
| 9 | 0.78 | 6.25 | 12.5 | 12.5 | 0.39 | 12.5 | 50 | 12.5 |
| 12 | 0.39 | 6.25 | 6.25 | 6.25 | 0.1 | 6.25 | 50 | 12.5 |
| 13 | 0.39 | 6.25 | 6.25 | 3.13 | 0.2 | 6.25 | 50 | 12.5 |
| 14 | 0.39 | 6.25 | 6.25 | 6.25 | 0.1 | 6.25 | 50 | 12.5 |
| 15 | 0.39 | 6.25 | 12.5 | 3.13 | 0.1 | 6.25 | 50 | 6.25 |
| 16 | 0.39 | 6.25 | 6.25 | 3.13 | 0.2 | 6.25 | 50 | 6.25 |
| 17 | 0.39 | 6.25 | 6.25 | 3.13 | 0.1 | 6.25 | 50 | 12.5 |
| 18 | 0.39 | 6.25 | 6.25 | 6.25 | 0.2 | 6.25 | 50 | 12.5 |
| 19 | 0.39 | 6.25 | 12.5 | 6.25 | 0.2 | 12.5 | 50 | 25 |
| 20 | 0.78 | 3.13 | 3.13 | 1.56 | 0.1 | 3.13 | 12.5 | 3.13 |
| 21 | 0.78 | 3.13 | 3.13 | 1.56 | 0.2 | 3.13 | 12.5 | 3.13 |
| 22 | 0.78 | 6.25 | 1.56 | 1.56 | 0.1 | 3.13 | 12.5 | 3.13 |
| 23 | 1.56 | 6.25 | 3.13 | 1.56 | 0.2 | 3.13 | 12.5 | 3.13 |
| 24 | 1.56 | 6.25 | 3.13 | 1.56 | 0.39 | 3.13 | 12.5 | 3.13 |
| 25 | 1.56 | 6.25 | 3.13 | 3.13 | 0.39 | 3.13 | 12.5 | 6.25 |
| 26 | 1.56 | 6.25 | 3.13 | 3.13 | 0.2 | 3.13 | 12.5 | 6.25 |
| 27 | 1.56 | 6.25 | 3.13 | 1.56 | 0.2 | 3.13 | 12.5 | 3.13 |
| 28 | 1.56 | 6.25 | 1.56 | 1.56 | 0.1 | 3.13 | 12.5 | 3.13 |
| 29 | 0.78 | 6.25 | 1.56 | 1.56 | 0.2 | 3.13 | 12.5 | 3.13 |
| 31 | 0.78 | 6.25 | 3.13 | 3.13 | 0.39 | 6.25 | 50 | 25 |
| 32 | 0.78 | 6.25 | 3.13 | 3.13 | 0.39 | 6.25 | 50 | 12.5 |
| 33 | 0.78 | 6.25 | 3.13 | 3.13 | 0.78 | 6.25 | 50 | 12.5 |
| 34 | 0.78 | 6.25 | 3.13 | 3.13 | 0.78 | 6.25 | 50 | 12.5 |
| 35 | 1.56 | 6.25 | 6.25 | 3.13 | 0.39 | 6.25 | 50 | 25 |
| 36 | 0.78 | 6.25 | 3.13 | 1.56 | 0.2 | 3.13 | 12.5 | 6.25 |
| 37 | 0.78 | 6.25 | 1.56 | 1.56 | 0.2 | 3.13 | 12.5 | 6.25 |
| 38 | 0.78 | 6.25 | 1.56 | 1.56 | 0.1 | 3.13 | 12.5 | 3.13 |
| 39 | 0.78 | 6.25 | 1.56 | 1.56 | 0.1 | 3.13 | 12.5 | 3.13 |
| 40 | 0.78 | 6.25 | 3.13 | 1.56 | 0.1 | 3.13 | 12.5 | 6.25 |
| 41 | 1.56 | 6.25 | 3.13 | 3.13 | 0.2 | 6.25 | 12.5 | 6.25 |
| 42 | 1.56 | 6.25 | 3.13 | 3.13 | 0.2 | 6.25 | 12.5 | 6.25 |
| 43 | 0.78 | 6.25 | 6.25 | 3.13 | 0.39 | 6.25 | 12.5 | 6.25 |
| 44 | 0.78 | 6.25 | 6.25 | 3.13 | 0.39 | 6.25 | 12.5 | 6.25 |
| 45 | 0.39 | 6.25 | 12.5 | 3.13 | 0.39 | 12.5 | 50 | 12.5 |
| 46 | 0.78 | 6.25 | 12.5 | 3.13 | 0.39 | 12.5 | 50 | 12.5 |
| 47 | 0.78 | 6.25 | 12.5 | 3.13 | 0.39 | 12.5 | 50 | 12.5 |
| 48 | 0.78 | 12.5 | 12.5 | 3.13 | 0.78 | 25 | 100 | 25 |
| 49 | 0.78 | 12.5 | 12.5 | 6.25 | 0.78 | 25 | 50 | 25 |
| 50 | 1.56 | 6.25 | 3.13 | 3.13 | 0.39 | 6.25 | 50 | 6.25 |
| 51 | 0.39 | 3.13 | 12.5 | 12.5 | 0.2 | 6.25 | >200 | 25 |
| 52 | 1.56 | 6.25 | 1.56 | 3.13 | 0.1 | 6.25 | 12.5 | 3.13 |
| 53 | 1.56 | 6.25 | 3.13 | 1.56 | 0.39 | 6.25 | 50 | 6.25 |
| 54 | 0.78 | 6.25 | 1.56 | 3.13 | 0.1 | 3.13 | 12.5 | 3.13 |
| 55 | 0.78 | 3.13 | 1.56 | 3.13 | 0.1 | 3.13 | 12.5 | 3.13 |
| 56 | 0.39 | 6.25 | 6.25 | 6.25 | 0.1 | 6.25 | 50 | 12.5 |
| 57 | 0.39 | 6.25 | 6.25 | 6.25 | 0.1 | 6.25 | 50 | 12.5 |
| 58 | 0.39 | 3.13 | 12.5 | 12.5 | 0.2 | 6.25 | >200 | 25 |
| 59 | 0.39 | 6.25 | 6.25 | 6.25 | 0.1 | 6.25 | 50 | 12.5 |
| 60 | 0.39 | 6.25 | 6.25 | 6.25 | 0.1 | 6.25 | 50 | 12.5 |
| 61 | 0.39 | 6.25 | 25 | 12.5 | 0.2 | 6.25 | >200 | 25 |
| 62 | 1.56 | 6.25 | 12.5 | 3.13 | 0.39 | 6.25 | 100 | 25 |
| 63 | 1.56 | 6.25 | 6.25 | 1.56 | 0.1 | 6.25 | 50 | 12.5 |
| 64 | 1.56 | 6.25 | 1.56 | 3.13 | 0.1 | 6.25 | 12.5 | 3.13 |

-continued

| | Minimum Inhibitory Concentration (μg/ml) | | | | | | | |
|---|---|---|---|---|---|---|---|---|
| Example No. | Staphylococcus aureus 209 P | Staphylococcus aureus* FS 289 | Escherichia coli NIHJ | Klebsiella pneumoniae 602 | Proteus vulgaris HX 19 | Pseudomonas aeruginosa 104 | Serratia No.72 | Enterobacter aerogeneus No.75 |
| 65 | 0.78 | 6.25 | 3.13 | 3.13 | 0.2 | 3.13 | 12.5 | 3.13 |
| 66 | 0.78 | 6.25 | 3.13 | 3.13 | 0.1 | 3.13 | 12.5 | 3.13 |
| 67 | 0.78 | 3.13 | 1.56 | 3.13 | 0.1 | 3.13 | 12.5 | 3.13 |
| 68 | 0.78 | 3.13 | 1.56 | 3.13 | 0.1 | 3.13 | 12.5 | 3.13 |
| 69 | 0.39 | 6.25 | 6.25 | 6.25 | 0.2 | 6.25 | 50 | 12.5 |
| 70 | 1.56 | 6.25 | 3.13 | 3.13 | 0.1 | 6.25 | 12.5 | 6.25 |
| 71 | 1.56 | 6.25 | 1.56 | 3.13 | 0.1 | 3.13 | 12.5 | 3.13 |
| 72 | 0.78 | 6.25 | 3.13 | 6.25 | 0.2 | 6.25 | 50 | 12.5 |
| 73 | 0.78 | 6.25 | 6.25 | 3.13 | 0.2 | 6.25 | 25 | 6.25 |
| 74 | 0.78 | 6.25 | 1.56 | 3.13 | 0.1 | 3.13 | 12.5 | 6.25 |
| 75 | 1.56 | 12.5 | 6.25 | 3.13 | 0.39 | 6.25 | 25 | 12.5 |
| 76 | 0.78 | 6.25 | 3.13 | 3.13 | 0.2 | 3.13 | 12.5 | 3.13 |
| 77 | 0.78 | 6.25 | 3.13 | 3.13 | 0.1 | 3.13 | 12.5 | 3.13 |
| 78 | 0.78 | 6.25 | 3.13 | 3.13 | 0.2 | 3.13 | 12.5 | 6.25 |
| 79 | 0.78 | 12.5 | 6.25 | 3.13 | 0.2 | 3.13 | 12.5 | 6.25 |
| 80 | 0.78 | 6.25 | 3.13 | 3.13 | 0.2 | 3.13 | 12.5 | 3.13 |
| 81 | 1.56 | 6.25 | 1.56 | 3.13 | 0.1 | 3.13 | 12.5 | 3.13 |
| 82 | 0.78 | 6.25 | 3.13 | 1.56 | 0.1 | 3.13 | 12.5 | 3.13 |
| 83 | 0.39 | 6.25 | 6.25 | 6.25 | 0.2 | 6.25 | 50 | 12.5 |
| 84 | 0.39 | 6.25 | 6.25 | 3.13 | 0.2 | 6.25 | 50 | 12.5 |
| 85 | 0.39 | 6.25 | 6.25 | 3.13 | 0.2 | 6.25 | 100 | 25 |
| 86 | 0.78 | 6.25 | 12.5 | 6.25 | 0.39 | 12.5 | 50 | 12.5 |
| 87 | 0.78 | 6.25 | 12.5 | 6.25 | 0.78 | 12.5 | 50 | 12.5 |
| 88 | 0.78 | 6.25 | 25 | 25 | 0.39 | 12.5 | >200 | 25 |
| 89 | 1.56 | 6.25 | 3.13 | 1.56 | 0.78 | 6.25 | 50 | 6.25 |
| 90 | 0.78 | 6.25 | 12.5 | 25 | 0.39 | 12.5 | >200 | 12.5 |
| 91 | 0.78 | 6.25 | 12.5 | 12.5 | 0.39 | 12.5 | 50 | 25 |
| 92 | 0.78 | 6.25 | 25 | 12.5 | 0.39 | 12.5 | >200 | 25 |
| 93 | 0.78 | 12.5 | 12.5 | 12.5 | 0.2 | 12.5 | 50 | 25 |
| 94 | 0.78 | 12.5 | 25 | 12.5 | 0.78 | 25 | 50 | 25 |
| 95 | 0.78 | 12.5 | 25 | 12.5 | 0.78 | 25 | 50 | 25 |
| 96 | 1.56 | 6.25 | 3.13 | 1.56 | 0.2 | 6.25 | 12.5 | 6.25 |
| 97 | 1.56 | 6.25 | 1.56 | 1.56 | 0.2 | 6.25 | 25 | 6.25 |
| 98 | 1.56 | 6.25 | 1.56 | 1.56 | 0.2 | 6.25 | 25 | 6.25 |
| 99 | 1.56 | 6.25 | 6.25 | 6.25 | 0.78 | 12.5 | 50 | 12.5 |
| 100 | 1.56 | 6.25 | 3.13 | 6.25 | 0.39 | 6.25 | 50 | 6.25 |
| 102 | 1.56 | 6.25 | 3.13 | 3.13 | 0.39 | 6.25 | 25 | 12.5 |
| 103 | 1.56 | 6.25 | 3.13 | 3.13 | 0.2 | 6.25 | 12.5 | 12.5 |
| 104 | 1.56 | 6.25 | 6.25 | 3.13 | 0.39 | 6.25 | 12.5 | 12.5 |
| 105 | 0.78 | 6.25 | 6.25 | 3.13 | 0.2 | 6.25 | 12.5 | 12.5 |
| 106 | 1.56 | 6.25 | 3.13 | 1.56 | 0.2 | 6.25 | 12.5 | 6.25 |
| 107 | 1.56 | 6.25 | 3.13 | 1.56 | 0.1 | 6.25 | 12.5 | 6.25 |
| 108 | 1.56 | 12.5 | 3.13 | 3.13 | 0.2 | 6.25 | 25 | 6.25 |
| 109 | 1.56 | 12.5 | 6.25 | 6.25 | 0.78 | 12.5 | 50 | 12.5 |
| 110 | 0.78 | 6.25 | 12.5 | 12.5 | 0.39 | 12.5 | 100 | 25 |
| 111 | 0.78 | 6.25 | 12.5 | 6.25 | 0.39 | 12.5 | 100 | 12.5 |
| 112 | 0.78 | 12.5 | 12.5 | 6.25 | 0.78 | 12.5 | 100 | 25 |
| 113 | 0.39 | 3.13 | 12.5 | 12.5 | 0.2 | 6.25 | >200 | 25 |
| 114 | 0.39 | 6.25 | 12.5 | 12.5 | 0.39 | 6.25 | >200 | 25 |
| 115 | 0.39 | 6.25 | 12.5 | 25 | 0.78 | 12.5 | >200 | 25 |
| 116 | 0.39 | 3.13 | 12.5 | 6.25 | 0.2 | 6.25 | >200 | 25 |
| 117 | 0.39 | 6.25 | 12.5 | 12.5 | 0.2 | 6.25 | 100 | 25 |
| 118 | 0.39 | 6.25 | 12.5 | 25 | 0.39 | 6.25 | >200 | 25 |
| 119 | 0.39 | 6.25 | 6.25 | 25 | 0.39 | 6.25 | >200 | 25 |
| 120 | 0.78 | 6.25 | 3.13 | 1.56 | 0.39 | 6.25 | 50 | 6.25 |
| 122 | 0.78 | 6.25 | 3.13 | 3.13 | 0.39 | 6.25 | 50 | 6.25 |
| 123 | 0.78 | 6.25 | 6.25 | 3.13 | 0.78 | 6.25 | 100 | 12.5 |
| 124 | 0.78 | 6.25 | 12.5 | 12.5 | 0.78 | 12.5 | 100 | 25 |
| 125 | 0.39 | 6.25 | 6.25 | 6.25 | 0.1 | 12.5 | 50 | 12.5 |
| 126 | 0.39 | 6.25 | 6.25 | 12.5 | 0.2 | 6.25 | 100 | 12.5 |
| 127 | 0.39 | 6.25 | 6.25 | 6.25 | 0.2 | 6.25 | 50 | 12.5 |
| 128 | 0.39 | 6.25 | 6.25 | 6.25 | 0.39 | 6.25 | 50 | 12.5 |
| 129 | 0.78 | 3.13 | 1.56 | 1.56 | 0.1 | 3.13 | 12.5 | 3.13 |
| 130 | 0.78 | 3.13 | 1.56 | 1.56 | 0.1 | 3.13 | 12.5 | 3.13 |
| 131 | 0.78 | 3.13 | 1.56 | 0.78 | 0.1 | 3.13 | 12.5 | 3.13 |
| 132 | 0.78 | 3.13 | 3.13 | 1.56 | 0.1 | 6.25 | 25 | 3.13 |
| 133 | 0.78 | 3.13 | 3.13 | 1.56 | 0.1 | 3.13 | 25 | 3.13 |
| 134 | 0.78 | 3.13 | 3.13 | 1.56 | 0.1 | 3.13 | 25 | 3.13 |
| 136 | 0.78 | 6.25 | 3.13 | 3.13 | 0.78 | 6.25 | 100 | 6.25 |
| 137 | 1.56 | 12.5 | 12.5 | 12.5 | 1.56 | 12.5 | 100 | 50 |
| 138 | 0.78 | 6.25 | 3.13 | 1.56 | 0.78 | 6.25 | 50 | 6.25 |
| 139 | 1.56 | 12.5 | 12.5 | 6.25 | 3.13 | 12.5 | 50 | 50 |
| 140 | 0.78 | 6.25 | 3.13 | 6.25 | 1.56 | 6.25 | 50 | 12.5 |
| 141 | 0.78 | 6.25 | 6.25 | 6.25 | 0.78 | 6.25 | 50 | 12.5 |
| 142 | 1.56 | 6.25 | 3.13 | 3.13 | 0.78 | 6.25 | 50 | 6.25 |
| 143 | 3.13 | 12.5 | 6.25 | 3.13 | 0.78 | 6.25 | 100 | 12.5 |
| 144 | 3.13 | 12.5 | 6.25 | 6.25 | 1.56 | 6.25 | 100 | 12.5 |

-continued

| Example No. | Staphylococcus aureus 209 P | Staphylococcus aureus* FS 289 | Escherichia coli NIHJ | Klebsiella pneumoniae 602 | Proteus vulgaris HX 19 | Pseudomonas aeruginosa 104 | Serratia No.72 | Enterobacter aerogeneus No.75 |
|---|---|---|---|---|---|---|---|---|
| Minimum Inhibitory Concentration (μg/ml) | | | | | | | | |
| 145 | 0.78 | 6.25 | 3.13 | 3.13 | 0.39 | 6.25 | 100 | 12.5 |
| 146 | 0.78 | 12.5 | 1.56 | 3.13 | 1.56 | 3.13 | 25 | 6.25 |
| 147 | 1.56 | 12.5 | 3.13 | 3.13 | 1.56 | 3.13 | 25 | 6.25 |
| 148 | 1.56 | 12.5 | 3.13 | 3.13 | 1.56 | 3.13 | 25 | 6.25 |
| 149 | 0.78 | 6.25 | 3.13 | 3.13 | 0.39 | 6.25 | 25 | 6.25 |
| 150 | 0.78 | 6.25 | 3.13 | 1.56 | 0.2 | 3.13 | 12.5 | 6.25 |
| 151 | 0.78 | 6.25 | 1.56 | 1.56 | 0.39 | 6.25 | 12.5 | 6.25 |
| 152 | 0.78 | 6.25 | 3.13 | 1.56 | 0.2 | 3.13 | 12.5 | 6.25 |
| 153 | 0.78 | 6.25 | 3.13 | 3.13 | 0.39 | 6.25 | 25 | 6.25 |
| 154 | 0.78 | 12.5 | 3.13 | 6.25 | 0.39 | 3.13 | 12.5 | 6.25 |
| 155 | 0.78 | 12.5 | 3.13 | 6.25 | 0.78 | 3.13 | 12.5 | 6.25 |
| 156 | 1.56 | 12.5 | 6.25 | 6.25 | 0.78 | 6.25 | 50 | 12.5 |
| 157 | 1.56 | 12.5 | 3.13 | 3.13 | 0.2 | 6.25 | 25 | 6.25 |
| 158 | 0.39 | 12.5 | 6.25 | 1.56 | 0.39 | 6.25 | 25 | 12.5 |
| 159 | 0.39 | 12.5 | 6.25 | 3.13 | 0.78 | 6.25 | 50 | 12.5 |
| 160 | 0.78 | 12.5 | 12.5 | 6.25 | 1.56 | 12.5 | 50 | 12.5 |
| 161 | 0.78 | 12.5 | 6.25 | 3.13 | 0.39 | 6.25 | 50 | 12.5 |
| 162 | 1.56 | 12.5 | 12.5 | 6.25 | 0.78 | 6.25 | 50 | 25 |
| 163 | 1.56 | 12.5 | 12.5 | 6.25 | 0.39 | 6.25 | 50 | 25 |
| 164 | 0.78 | 6.25 | 3.13 | 1.56 | 0.2 | 3.13 | 12.5 | 3.13 |
| 165 | 0.78 | 6.25 | 3.13 | 3.13 | 0.2 | 3.13 | 12.5 | 6.25 |
| 166 | 0.78 | 6.25 | 3.13 | 1.56 | 0.2 | 3.13 | 12.5 | 3.13 |
| 167 | 1.56 | 6.25 | 1.56 | 1.56 | 0.2 | 3.13 | 12.5 | 3.13 |
| 168 | 1.56 | 12.5 | 12.5 | 6.25 | 0.78 | 12.5 | 50 | 25 |
| 169 | 0.78 | 6.25 | 3.13 | 1.56 | 0.1 | 3.13 | 25 | 3.13 |
| 170 | 0.78 | 6.25 | 6.25 | 1.56 | 0.1 | 3.13 | 25 | 6.25 |
| 171 | 1.56 | 12.5 | 3.13 | 1.56 | 0.2 | 3.13 | 25 | 3.13 |
| 172 | 0.78 | 12.5 | 3.13 | 3.13 | 0.78 | 6.25 | 25 | 6.25 |
| 173 | 0.78 | 12.5 | 12.5 | 6.25 | 0.78 | 6.25 | 50 | 25 |
| 174 | 0.78 | 12.5 | 3.13 | 1.56 | 0.39 | 3.13 | 12.5 | 3.13 |
| 175 | 0.78 | 12.5 | 3.13 | 3.13 | 0.39 | 3.13 | 12.5 | 6.25 |
| 176 | 0.39 | 6.25 | 6.25 | 6.25 | 0.2 | 12.5 | 50 | 12.5 |
| 177 | 0.39 | 6.25 | 6.25 | 6.25 | 0.2 | 12.5 | 100 | 12.5 |
| 178 | 0.78 | 6.25 | 3.13 | 1.56 | 0.2 | 3.13 | 12.5 | 6.25 |
| 179 | 0.39 | 6.25 | 6.25 | 6.25 | 0.39 | 12.5 | 50 | 12.5 |
| 180 | 0.78 | 6.25 | 3.13 | 1.56 | 0.1 | 3.13 | 12.5 | 3.13 |
| 181 | 0.78 | 6.25 | 1.56 | 1.56 | 0.2 | 3.13 | 12.5 | 6.25 |
| 182 | 0.78 | 3.13 | 12.5 | 25 | 0.78 | 12.5 | >200 | 25 |
| 183 | 0.78 | 6.25 | 6.25 | 12.5 | 0.39 | 6.25 | 50 | 12.5 |
| 184 | 0.78 | 6.25 | 6.25 | 12.5 | 0.78 | 6.25 | 50 | 12.5 |
| 185 | 0.78 | 6.25 | 6.25 | 6.25 | 0.39 | 6.25 | 50 | 12.5 |
| 186 | 0.78 | 6.25 | 6.25 | 12.5 | 0.78 | 12.5 | 50 | 12.5 |
| 187 | 0.78 | 6.25 | 6.25 | 12.5 | 0.39 | 6.25 | 50 | 12.5 |
| Known Compounds | | | | | | | | |
| CEG | 1.56 | 12.5 | 12.5 | 3.13 | 12.5 | >200 | >200 | 50 |
| CET | 0.1 | 0.78 | 12.5 | 0.78 | 3.13 | >200 | >200 | >200 |
| CEZ | 0.2 | 1.56 | 1.56 | 0.78 | 6.25 | >200 | >200 | 100 |

*Staphylococcus aureus FS 289: strain resistant to penicillin

CEG (Cephaloglycin)

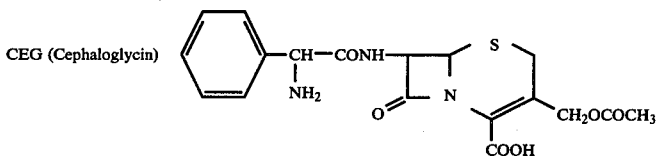

CET (Cephalothin)

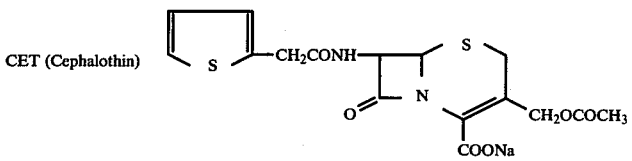

CEZ (Cefazolin)

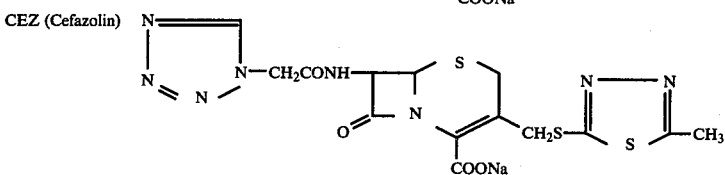

While the invention has been described in detail and with reference to specific embodiments thereof, it will be apparent to one skilled in the art that various changes aand modifications can be made therein without departing from the spirit and scope thereof.

What is claimed is:

1. A compound of the formula,

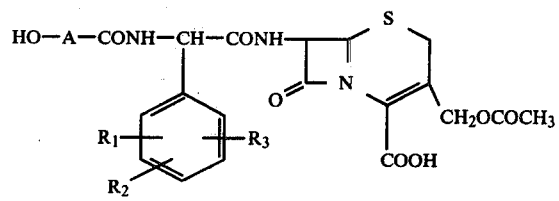

wherein A is cinnoline, naphthyridine, pyridopyrazine, thiazolopyrimidine, pyridopyrimidine, pyridine, pyrimidine, or pyridazine, each of which can be substituted with one or more substituents selected from the group consisting of a $(C_1-C_4)$alkyl group, a $(C_1-C_4)$alkoxy group, a $(C_1-C_4)$alkylthio group and a hydroxy group and wherein the hydroxy group attached to A is ortho to the amido group attached to A; $R_1$ is an amino group, a hydroxy group, a hydroxymethyl group or a ureido group; and $R_2$ and $R_3$, which may be the same or different, each is chloro, fluoro, methoxy or hydroxy, and the non-toxic pharmaceutically acceptable salts thereof.

* * * * *